United States Patent
Lee et al.

(10) Patent No.: US 11,020,196 B2
(45) Date of Patent: Jun. 1, 2021

(54) INSTRUMENT SHAFT FOR COMPUTER-ASSISTED SURGICAL SYSTEM

(71) Applicant: INTUITIVE SURGICAL OPERATIONS, INC., Sunnyvale, CA (US)

(72) Inventors: Peling G. Lee, Palo Alto, CA (US); Theodore W. Rogers, Alameda, CA (US); John Ryan Steger, Sunnyvale, CA (US); Matthew R. Williams, Walnut Creek, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 178 days.

(21) Appl. No.: 16/171,942

(22) Filed: Oct. 26, 2018

(65) Prior Publication Data
US 2019/0060017 A1  Feb. 28, 2019

Related U.S. Application Data

(63) Continuation of application No. 14/911,977, filed as application No. PCT/US2014/051140 on Aug. 14, 2014, now Pat. No. 10,130,437.
(Continued)

(51) Int. Cl.
*A61B 34/00*  (2016.01)
*A61B 18/14*  (2006.01)
(Continued)

(52) U.S. Cl.
CPC .......... *A61B 34/71* (2016.02); *A61B 18/1445* (2013.01); *A61B 34/30* (2016.02);
(Continued)

(58) Field of Classification Search
CPC ..... A61B 34/30; A61B 34/71; A61B 18/1445; A61B 2017/2901; A61B 2017/2902; A61B 2017/2948; A61B 2034/302
See application file for complete search history.

(56) References Cited

U.S. PATENT DOCUMENTS 6,331,181 B1   12/2001   Tierney et al.
6,394,998 B1   5/2002    Wallace et al.
(Continued)

FOREIGN PATENT DOCUMENTS

WO   WO-2009120944 A2   10/2009

OTHER PUBLICATIONS

International Search Report and Written Opinion for Application No. PCT/US14/51140, dated Nov. 26, 2014, 22 pages.
(Continued)

*Primary Examiner* — Robert A Lynch
(74) *Attorney, Agent, or Firm* — Jones Robb, PLLC

(57) ABSTRACT

A shaft for a surgical instrument comprises an outer tube having a proximal end and a distal end, a central lumen extending through the outer tube, and a plurality of stiffening rods positioned around the central lumen. The plurality of stiffening rods may comprise a nonconductive material. The shaft may form part of an electrosurgical instrument. In another embodiment, a surgical instrument may comprise an end effector and a shaft having an outer tube having a proximal end and a distal end, a drive rod, and at least four stiffening rods positioned around the drive rod, each stiffening rod being positioned substantially immediately adjacent to the drive rod. The axial stiffness of the shaft increases incrementally during actuation of the end effector.

19 Claims, 19 Drawing Sheets

Related U.S. Application Data

(60) Provisional application No. 61/866,367, filed on Aug. 15, 2013.

(51) Int. Cl.
*A61B 34/30* (2016.01)
*A61B 17/29* (2006.01)
*A61B 90/70* (2016.01)
*A61B 17/00* (2006.01)

(52) U.S. Cl.
CPC ..... *A61B 90/70* (2016.02); *A61B 2017/00544* (2013.01); *A61B 2017/2901* (2013.01); *A61B 2017/2948* (2013.01); *A61B 2034/302* (2016.02)

(56) References Cited

U.S. PATENT DOCUMENTS

| | | |
|---|---|---|
| 6,817,974 B2 | 11/2004 | Cooper et al. |
| 7,963,913 B2 | 6/2011 | Devengenzo et al. |
| 10,130,437 B2 | 11/2018 | Lee et al. |
| 2001/0021859 A1 | 9/2001 | Kawai et al. |
| 2007/0123855 A1 | 5/2007 | Morley et al. |
| 2008/0177283 A1 | 7/2008 | Lee et al. |
| 2009/0299343 A1* | 12/2009 | Rogers .............. A61B 1/0051 606/1 |
| 2010/0094083 A1 | 4/2010 | Taylor et al. |
| 2010/0280449 A1* | 11/2010 | Alvarez ............. A61B 34/30 604/95.04 |
| 2011/0071542 A1* | 3/2011 | Prisco ............... A61B 34/30 606/130 |
| 2012/0123395 A1 | 5/2012 | Stoy et al. |
| 2012/0215220 A1 | 8/2012 | Manzo et al. |
| 2014/0148759 A1* | 5/2014 | Macnamara ...... A61M 25/0147 604/95.04 |
| 2014/0338477 A1 | 11/2014 | Donlon et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INSTRUMENT SHAFT FOR COMPUTER-ASSISTED SURGICAL SYSTEM

This application is a continuation of U.S. patent application Ser. No. 14/911,977, filed Dec. 2, 2016, which is a national stage application of International PCT Application No. PCT/US2014/051140, filed internationally on Aug. 14, 2014, which claims the benefit of U.S. Provisional Application No. 61/866,367, filed on Aug. 15, 2013, each of which is incorporated by reference herein in its entirety.

TECHNICAL FIELD

Aspects of the present disclosure relate to a flexible shaft for a robotic surgical instrument. Aspects of the present disclosure also relate to a robotic surgical system that includes a surgical instrument having a flexible shaft with axial stiffening members.

INTRODUCTION

Benefits of minimally invasive surgery are well known, and include less patient trauma, less blood loss, and faster recovery times when compared to traditional, open incision surgery. In addition, the use of robotic surgical systems (e.g., teleoperated robotic systems that provide telepresence and computer-assisted surgical systems) are known. An example of a teleoperated robotic surgical system is the da Vinci® Surgical System manufactured by Intuitive Surgical, Inc. of Sunnyvale, Calif. Such surgical systems may allow a surgeon to operate with intuitive control and increased precision when compared to manual minimally invasive surgeries.

To further reduce patient trauma and to retain the benefits of teleoperated and computer-assisted surgical systems, surgeons have begun to carry out a surgical procedure to investigate or treat a patient's condition through a single incision through the skin. In some instances, such "single port access" surgeries have been performed with manual instruments or with existing surgical systems. In order to more effectively perform single port access surgeries, surgeons and computer-assisted surgical systems require tools and instruments that maximize the surgical space accessible through a single port and that maximize the number of surgical instruments that can access the port at one time.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a shaft for a surgical instrument is disclosed. The shaft comprises a shaft body having a proximal end and a distal end, a drive rod extending through the distal end of the shaft body, and an end effector operatively coupled to a distal end of the drive rod. The drive rod passes through a passageway in a clevis of the end effector, and the drive rod and passage are sized such that a maximum flow of air between the passage and the drive rod is 25 cc/min of air.

In accordance with another exemplary embodiment of the present disclosure, a method of sealing a shaft of a surgical instrument is provided. The method comprises positioning a drive rod in a shaft body of the surgical instrument, and connecting a distal end of the drive rod to an end effector of the surgical instrument. Connecting the distal end of the drive rod includes positioning the drive rod in a passageway of a clevis of the end effector, the passageway having a diameter configured to slidingly receive the drive rod. A diameter of the drive rod is between about 0.0000 inches and 0.0011 inches less than the diameter of the passageway.

In accordance with an alternative exemplary embodiment of the present disclosure, a shaft for a surgical instrument comprises an outer tube having a proximal end and a distal end, a central lumen extending through the outer tube, and a plurality of stiffening rods positioned around the central lumen. Each of the plurality of stiffening rods comprises a nonconductive material.

In accordance with yet another exemplary embodiment of the present disclosure, an electrosurgical instrument for a computer-assisted surgical system is provided. The instrument comprises a shaft, a drive rod, an electrosurgical end effector, and at least one stiffening rod configured to resist axial compression of the shaft during actuation of the end effector. The at least one stiffening rod comprises a nonconductive material.

In accordance with another exemplary embodiment of the present disclosure, a surgical instrument comprises a shaft having an outer tube having a proximal end and a distal end, a drive rod, and at least four stiffening rods positioned around the drive rod. Each stiffening rod is positioned substantially immediately adjacent to the drive rod. The surgical instrument further comprises an end effector operatively coupled to the drive rod. An axial stiffness of the shaft increases incrementally during actuation of the end effector.

In accordance with an alternative embodiment of the present teachings, a method of resisting axial compression in an instrument shaft is disclosed. The method comprises applying a first force to the instrument shaft sufficient to engage a first stiffening element contained within the shaft, the first stiffening element configured to resist axial compression of the shaft, and subsequently applying additional force to the instrument shaft sufficient to engage at least a second stiffening element contained within the shaft.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
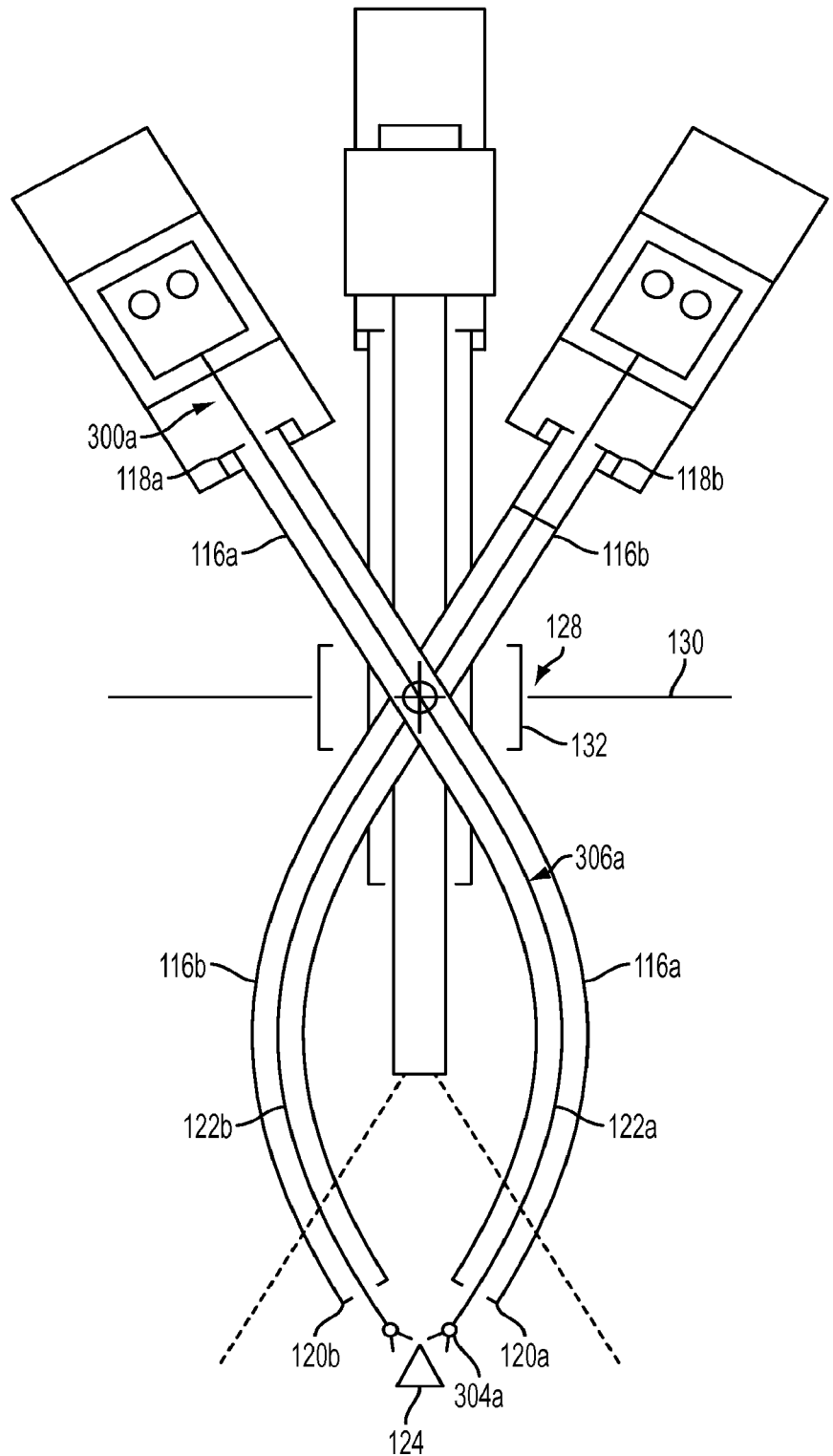
FIG. 1 is a schematic view that shows first and second curved cannulas and an endoscope for providing access to a surgical site through a single port.

This description and the accompanying drawings that illustrate exemplary embodiments should not be taken as limiting. Various mechanical, compositional, structural, electrical, and operational changes may be made without departing from the scope of this disclosure and the disclosed subject matter as claimed, including equivalents. In some instances, well-known structures and techniques have not been shown or described in detail so as not to obscure the disclosure. Like numbers in two or more figures represent the same or similar elements. Additionally, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure. For example, spatially relative terms—such as "proximal" and "distal"—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, the terms "proximal" and "distal" are relative terms, where the term "distal" refers to the portion of the object furthest from an operator of the instrument and closest to the surgical site, such as the opening of the tool cover or the end effector of the instrument. The term "proximal" indicates the relative proximity to the operator of the surgical instrument and refers to the portion of the object closest to the operator and furthest from the surgical site. In this application, an end effector refers to a tool installed at the distal end of an instrument, including but not limited to forceps or graspers, needle drivers, scalpels, scissors, spatulas, blades, and other tools, which may or may not use energy to cauterize tissue (i.e., a monopolar or bipolar tool).

The term "flexible" in association with a mechanical structure or component should be broadly construed. In essence, the term means the structure or component can be repeatedly bent and restored to an original shape without harm. Many "rigid" objects have a slight inherent resilient "bendiness" due to material properties, although such objects are not considered "flexible" as the term is used herein. A flexible mechanical structure may have infinite degrees of freedom (DOF's). Examples of such structures include closed, bendable tubes (made from, e.g., NITINOL, polymer, soft rubber, and the like), helical coil springs, etc.

that can be bent into various simple and compound curves, often without significant cross-sectional deformation. A short, flexible structure may serve as, and be modeled as, a single mechanical constraint (joint) that provides one or more DOF's between two links in a kinematic chain, even though the flexible structure itself may be a kinematic chain made of several coupled links. Knowledgeable persons will understand that a component's flexibility may be expressed in terms of its stiffness.

Aspects of the present disclosure are described primarily in terms of an implementation using a da Vinci® Surgical System, manufactured by Intuitive Surgical, Inc. of Sunnyvale, Calif. Knowledgeable persons will understand, however, that novel aspects disclosed herein may be embodied and implemented in various ways, including robotic and non-robotic embodiments and implementations. Implementations on da Vinci® Surgical Systems are merely exemplary and are not to be considered as limiting the scope of the novel aspects disclosed herein. The terms "robotic surgical system," "computer-assisted surgical system," "computer-assisted medical system," and "teleoperated surgical system" are used interchangeably herein to refer to a surgical system that includes aspects of computer-enabled function that may be autonomous, semiautonomous, or under direct teleoperated control. These systems may operate under direct manual control and/or may be teleoperated.

Various exemplary embodiments of the present disclosure contemplate a computer-assisted surgical system including an instrument having a flexible shaft permitting use in a curved cannula system such as those used in a single port access surgery. Single port access surgery is a technique in which all instruments used for minimally invasive surgery are passed through a single incision in the patient's body wall, or in some instances through a single natural orifice. Such methods may be referred to by various terms, such as Single Port Access (SPA), Laparo Endoscopic Single-site Surgery (LESS), Single Incision Laparoscopic Surgery (SILS), One Port Umbilical Surgery (OPUS), Single Port Incisionless Conventional Equipment-utilizing Surgery (SPICES), Single Access Site Surgical Endoscope (SASSE), or Natural Orifice TransUmbilical Surgery (NOTUS). Use of a single port may be accomplished using either manual instruments or a robotic surgical system.

An advantageous configuration for accessing a surgical site is to create a working triangle defined by the surgical site itself and the distal ends of two surgical instruments. In such a configuration, the distal ends of the surgical instruments are positioned along the legs of the triangle and above the apex of the triangle, the surgical site. In single port access surgeries, the use of a single port constrains the angle at which a surgical instrument can access the surgical site, making it difficult to achieve the desired triangulation between the distal ends of the surgical instruments and the surgical site itself.

One approach to maximize the surgical space available is to use a curved cannula system. Such curved cannula systems may be used with computer-assisted surgical systems or with other systems such as those used during manual surgery. Exemplary curved cannula systems are disclosed in detail in U.S. Published Application No. 2011/0071542 A1, published on Mar. 24, 2011, which is hereby incorporated by reference in its entirety. In contrast to the use of straight cannulas and instruments in a single body opening, the use of curved cannulas provides a reasonably large volume above the single incision in which instruments and/or robotic arms supporting instruments can move relative to one another without collision, providing a correspondingly larger volume in which the instruments can move at the surgical site.

FIG. 1 illustrates an exemplary pair of curved cannulas positioned for use in a single port access surgery. As shown, a port 132 may be placed in an incision 128 in a body wall 130 to provide access to surgical site 124. Cannulas extend through port 132 and surgical instruments passed through the cannulas can access the surgical site 124. Such a port 132 may have various configurations, as described in detail in U.S. Published Application No. 2011/0071542 A1, published on Mar. 24, 2011, and incorporated herein by reference in its entirety.

As shown in FIG. 1, first and second curved cannulas 116a, 116b each include a proximal end 118a, 118b, a distal end 120a, 120b, and a central channel 122a, 122b extending between proximal end 118a, 118b and distal end 120a, 120b. Curved cannulas 116a, 116b may be rigid, single piece cannulas. FIG. 1 illustrates that curved cannula 116b curves in a direction opposite to the direction in which curved cannula 116a curves. The two curved cannulas and associated surgical instruments are positioned to extend through single incision 128 in the patient's body wall 130 via port 128 to reach surgical site 124. Each curved cannula initially angles away from a straight line between the incision and the surgical site and then curves back towards the line to direct the extended instruments to the surgical site. Each curved cannula 116a, 116b provides an access pathway through the single port to the surgical site for a respective surgical instrument. During use, a flexible shaft 306a of a surgical instrument 300a extends through curved cannula 116a's central channel 122a so that a distal portion of flexible shaft 306a and the end effector 304a of the surgical instrument extend beyond cannula 116a's distal end 120a in order to reach surgical site 124.

Figure 2A:
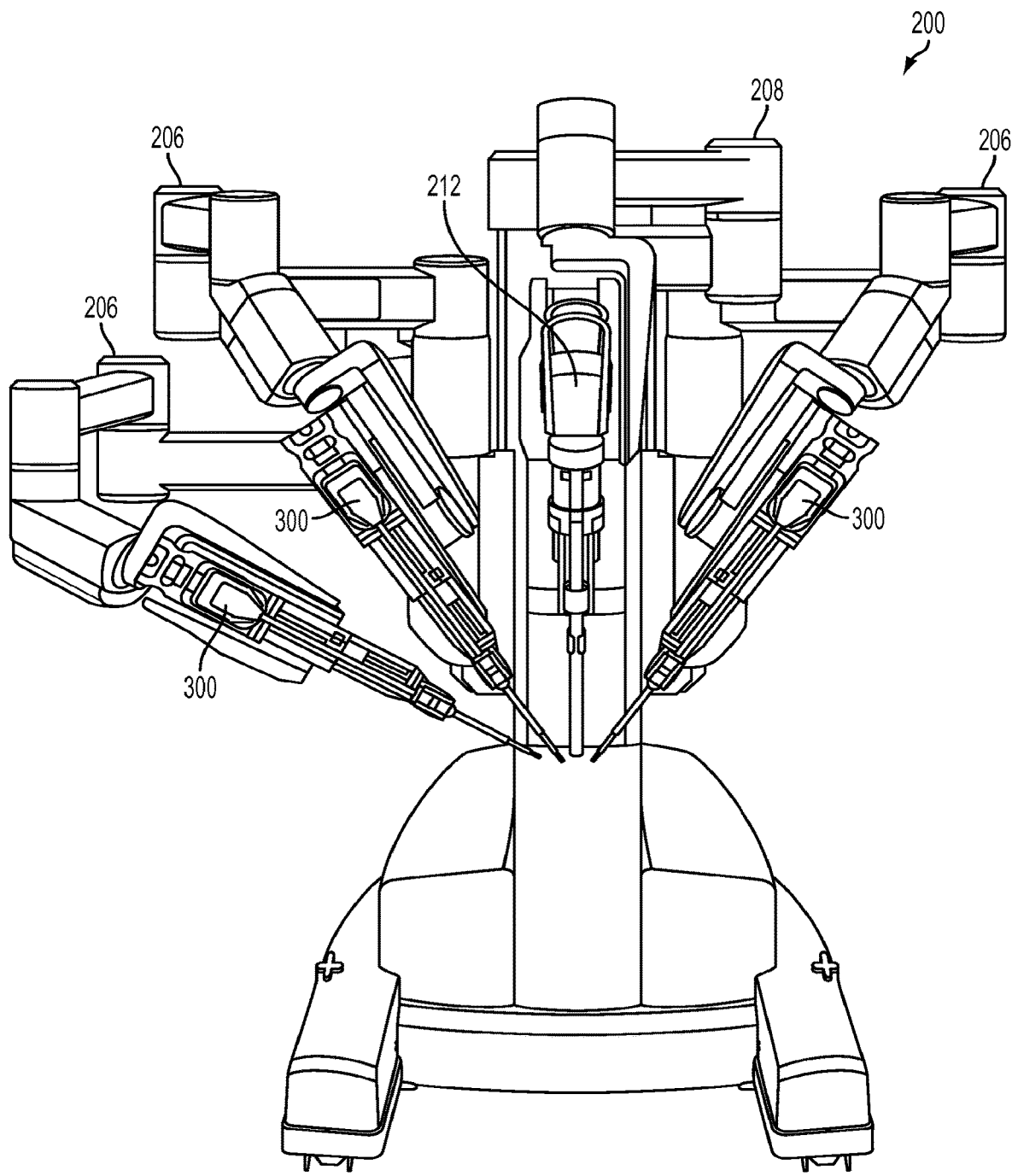
FIG. 2A is a front view of an exemplary embodiment of a portion of a teleoperated, computer-assisted surgical system.

FIG. 2A shows an exemplary teleoperated computer-assisted surgical system that can be used to support and move combinations of a curved cannula and a flexible surgical instrument to access a surgical site through a single port access in accordance with an embodiment of the present teachings. Such a teleoperated computer-assisted surgical system is described in U.S. Published Application No. 2011/0071542 A1, published on Mar. 24, 2011, which is hereby incorporated by reference in its entirety. Components of a teleoperated surgical system, such as an instrument arm, carriage, instrument interface, and other components, may have the features described in U.S. Pat. No. 7,963,913, issued Jun. 21, 2011, which is hereby incorporated by reference in its entirety. Such teleoperated, computer-assisted surgical systems include a processor and a memory.

The teleoperated computer-assisted surgical system 200 allows a surgeon, with the assistance of a surgical team, to perform diagnostic and corrective surgical procedures on a patient. In an exemplary embodiment, a teleoperated computer-assisted surgical system in accordance with the present disclosure may be embodied as a da Vinci® surgical system commercialized by Intuitive Surgical, Inc. of Sunnyvale, Calif. However, the present disclosure is not limited to any particular teleoperated computer-assisted surgical system, and one having ordinary skill in the art would appreciate that the disclosure herein may be applied in a variety of surgical applications, including other computer-assisted surgical systems, as well as in manual surgical applications.

System 200 includes a plurality of robotic arms 206, each of which supports and moves a combination of a curved cannula and a flexible surgical instrument. Each arm 206 is made of a series of links, the links being coupled to one another by joints. Arm 206 is divided into two portions, a "set-up" portion that positions the arm relative to the surgical site, and a patient side manipulator ("PSM") portion that supports and moves the curved cannula and surgical instrument relative to the surgical site. Flexible surgical instruments 300 can be interchangeably mounted on the manipulator portion of arm 206. In this manner, instruments 300 can be selected for a particular medical procedure or changed during a medical procedure to provide the clinical functions needed.

Figure 3:
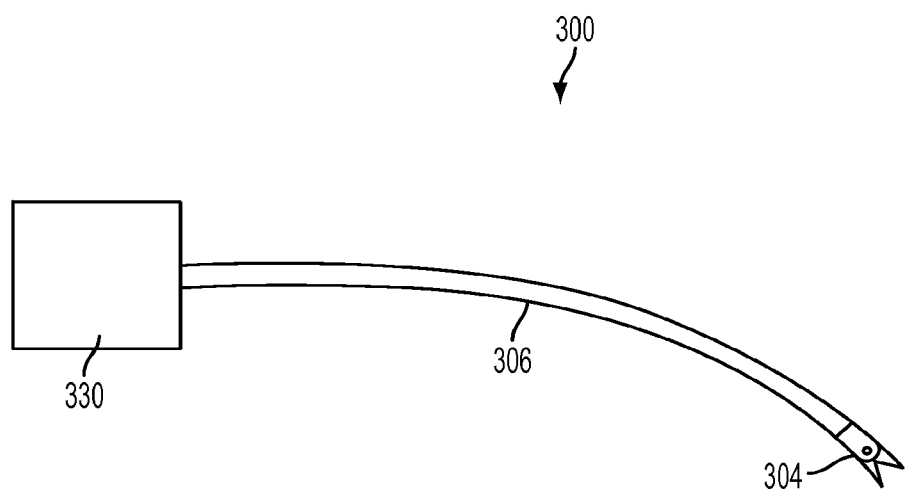
FIG. 3 is a side view of a flexible surgical instrument in accordance with the present teachings.

As illustrated in FIG. 3, a flexible surgical instrument 300 generally includes a transmission or backend mechanism 330, a shaft 306 extending from the backend mechanism 330, and a distal end effector 304 extending from the distal end of the shaft 306. In some cases, a wrist (not shown) may connect shaft 306 and end effector 304. A drive rod that is connected to end effector 304 (or to a wrist) in an instrument 300 may extend through shaft 306 and connect to backend mechanism 330. Backend mechanism 330 typically provides a mechanical coupling of the drive rod to a drive motor in system 200. System 200 can thus control movement of the drive rod as needed to move or position and operate distal end effector 304. Actuation forces may typically roll instrument shaft 306, operate a wrist to provide yaw and pitch DOF's, and operate a movable piece or grasping jaws of various end effectors (e.g., scissors (cautery or non-cautery capable), dissectors, graspers, needle drivers, electrocautery hooks, retractors, clip appliers, etc.). According to an exemplary embodiment, surgical tools may be arranged according to the embodiments described in U.S. Pat. No. 6,817,974, issued Nov. 16, 2004, and U.S. Pat. No. 6,394,998, issued May 28, 2002, which are hereby incorporated by reference in their entirety.

System 200 also includes a camera arm 208 that supports and moves a camera system 212 such as an endoscope for viewing of a surgical site and the operation of instruments 300 within a patient. The views from the camera system, which may be stereoscopic or three-dimensional, can be viewed at a control console (not shown) and images may be displayed on a monitor (not shown). A processing system of system 200 can thus provide a user interface enabling a doctor or other medical personnel to see and manipulate the camera system and surgical instruments.

Figure 2B:
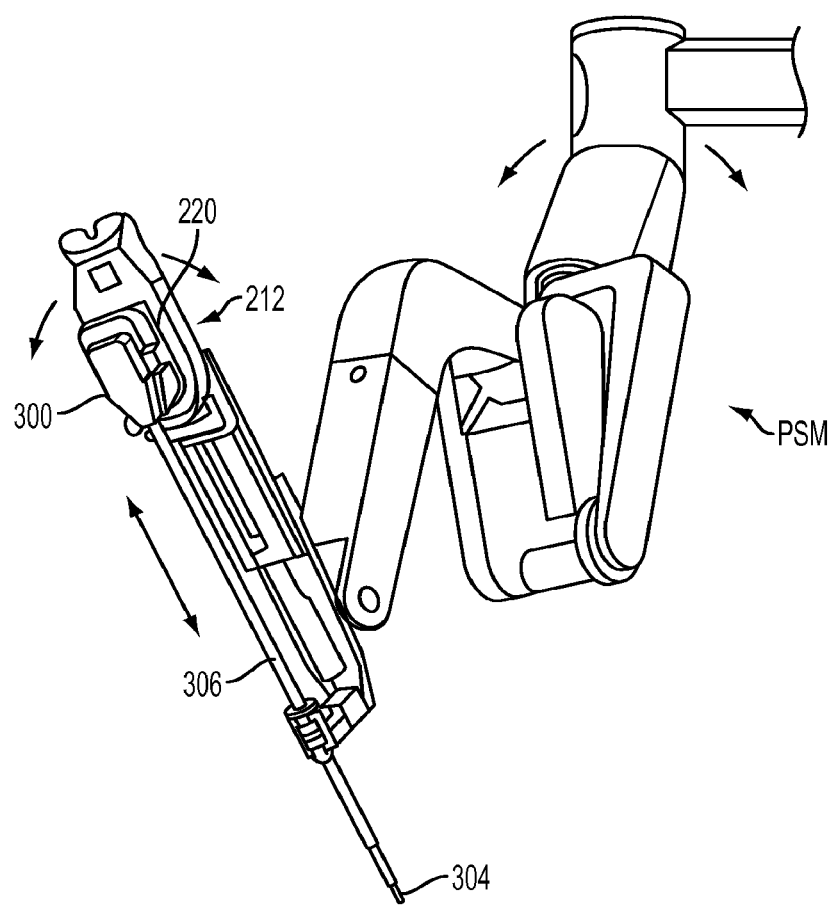
FIG. 2B is a perspective view of a patient side manipulator with a surgical instrument mounted thereon in accordance with the present teachings.

As illustrated in FIG. 2B, the patient side manipulator portion of arm 206 includes a carriage an instrument docking area 220 for releasably receiving a surgical instrument 300. Generally, the instrument docking area 220 releasably connects to a transmission mechanism 330 of surgical instrument 300. The PSM may include one or more drive motors that provide mechanical power for operation of surgical instruments 300. In addition, PSM may include an electrical interface for communication with a surgical instrument 300. Such communication may include reading a memory of a transmission mechanism 330 of a surgical instrument 300. Data included on the memory may include, for example, parameters relevant to a surgical instrument and its operation such as the type of instrument and/or specific characteristics of the instrument. High voltage electrical systems (not shown) such as generators for cauterizing or sealing instruments would typically connect to suitable instruments 300 through separate connectors but could alternatively be provided through built-in circuits in control system 200.

Figure 4A:
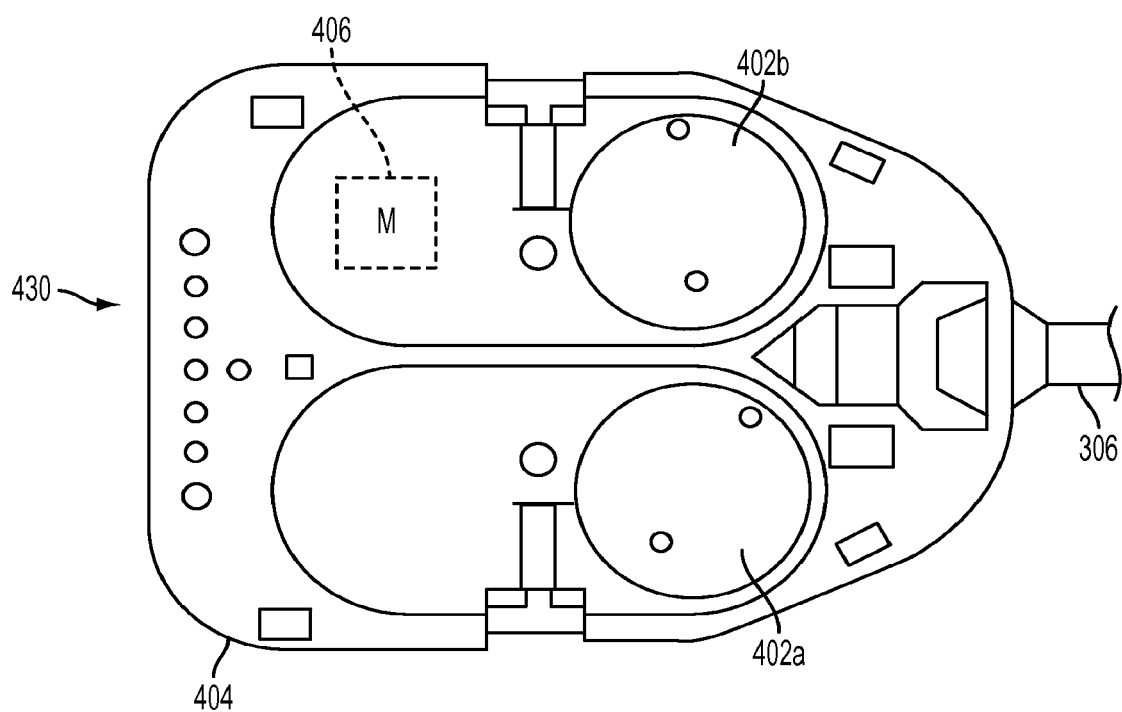
FIG. 4A is a bottom view of an exemplary embodiment of a force transmission mechanism for use with a flexible surgical instrument in accordance with the present teachings.

FIG. 4A is a bottom view of an exemplary embodiment of a force transmission mechanism 430. As shown in FIG. 4A, the force transmission mechanism 430 of a surgical instrument (not shown) used in a teleoperated surgical system has been modified to eliminate the mechanisms used to control a wrist mechanism on the instrument and to control the jaw of an end effector (or other moveable part) using only a single interface disk. Thus, in one illustrative implementation, one interface disk 402a rolls a shaft 306 of an instrument so as to provide a roll DOF for an end effector, and a second interface disk 402b may operate a jaw mechanism of an end effector to open and close the jaw mechanism. Force transmission mechanism 430 may be coupled to a PSM without any mechanical modifications required to the PSM, a feature that minimizes implementation costs of curved cannula aspects in existing teleoperated surgical systems. Further, each instrument may include a force transmission mechanism that permits control of the specific instrument without change to the interface between the PSM and the instrument.

Force transmission mechanism 430 may include electrically conductive interface pins 404 and an electronic data memory 406 that is electrically coupled to interface pins 404. Parameters relevant to a surgical instrument and its operation (e.g., number of times the instrument has been used, Denavit-Hartenberg parameters for control (described below), etc.) may be stored in memory 406 and accessed by the computer-assisted surgical system during operation to properly use the instrument (see e.g., U.S. Pat. No. 6,331,181 (issued Dec. 18, 2001) (disclosing surgical robotic tools, data architecture, and use), which is incorporated herein by reference in its entirety). Use of force transmission mechanisms for push/pull type instruments also is disclosed in U.S. Provisional Application No. 61/823,688 entitled "Force Transmission Mechanisms for Robotic Surgical Systems," filed May 15, 2013, the contents of which is incorporated herein by reference in its entirety.

In one implementation, kinematic data specific to a cannula through which the instrument extends may also be stored in memory 406, so that if the teleoperated surgical system detects that a particular cannula is mounted, the system may access and use the stored cannula data. If more than one cannula kinematic configuration (e.g., different lengths, bend radii, bend angles, etc.) is used, then data specific to each allowable configuration may be stored in the associated instrument's memory, and the system may access and use data for the specific cannula configuration that is mounted. In addition, if during a single port access surgery the robotic surgical system senses that an instrument intended for use with a curved cannula has been coupled to a manipulator that holds a straight, rather than curved, cannula, then the system may declare this situation to be an illegal state and prevent operation.

Figure 4B:
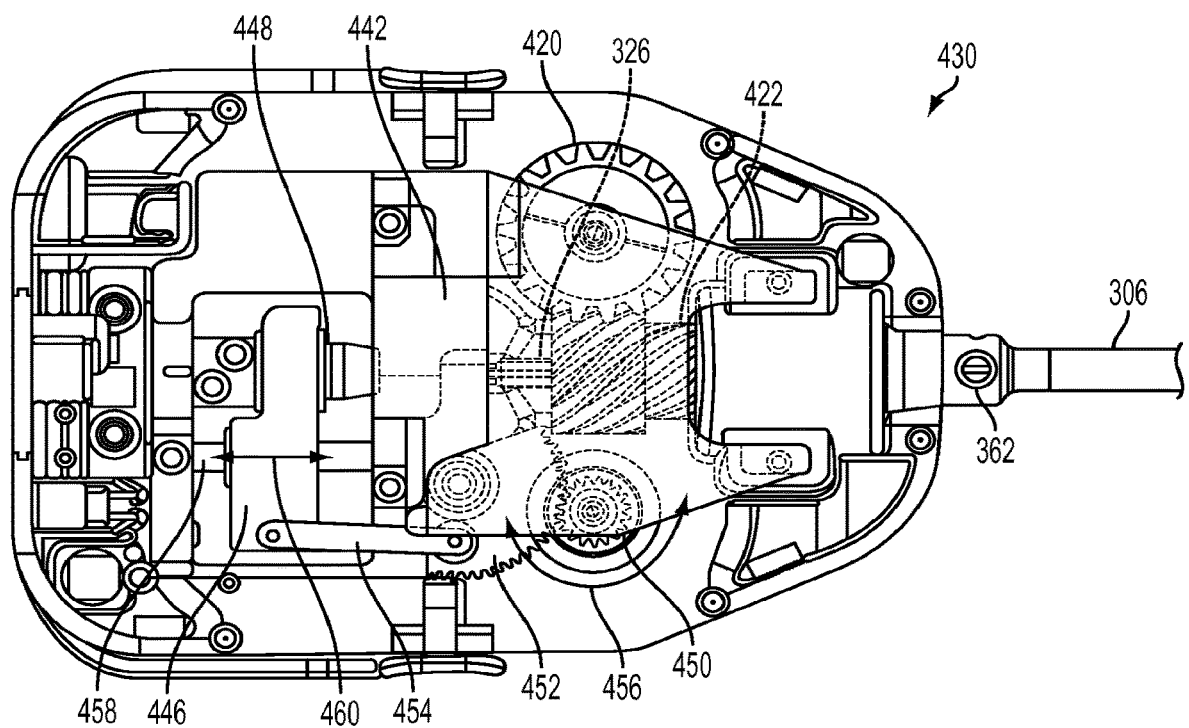
FIG. 4B is a plan view of an exemplary embodiment of a force transmission mechanism used in a push/pull flexible surgical instrument design in accordance with the present teachings.

FIG. 4B is a plan view of an exemplary embodiment of a force transmission mechanism used in a push/pull instrument design. As shown in FIG. 4B, a push/pull drive element rod 326 extends out of a proximal end of the instrument shaft 306, and further extends through a backing plate 442 to be coupled with slider 446. In this implementation, drive element rod 326 is coupled with linear slider 446 using a free rolling bearing 448. This free rolling bearing prevents the drive rod from twisting when the instrument shaft is rolled (i.e., provides an unconstrained roll DOF). Push/pull drive gear 450 is engaged with lever gear 452. Lever gear 452 is coupled to slider 446 with link (offset crank) 454. As drive gear 450 turns back and forth as indicated by arrows 456, slider 446 slides along shaft 458 as indicated by arrows 460, thus moving drive element 326 along the instrument shaft's longitudinal axis. FIG. 4B also shows a cross-connected helical drive gear 420 and a shaft roll gear 422. Roll gear 422 is coupled (e.g., laser welded) to a stainless steel adaptor swaged over the proximal end of the flexible shaft's body.

In accordance with the present teachings, a surgical instrument to be used in a single port access surgery and intended to pass through a curved cannula includes a flexible shaft. The shaft is relatively flexible to reduce friction with the inner wall of the curved cannula, yet it is not made so flexible so that it buckles during insertion through the curved cannula under manual or servo-controlled operation. While flexibility of the shaft is important, the shaft must be rigid enough to provide adequate cantilever support for the end effector (surgical tool). For instruments that require an end effector roll DOF via shaft roll, the shaft is torsionally rigid enough to transmit roll motion from the proximal end of the instrument to distal surgical end effector.

In particular, for any given bend radius of a curved cannula, a bending stiffness of a shaft in accordance with the present teachings falls within a range that balances the necessary flexibility to pass through the curved cannula with the stiffness required to apply useable force to the instrument end effector. Within this range, which varies dependent upon the curvature of the cannula to be traversed, the axial stiffness of the shaft is maximized through manipulation of various elements of the shaft, including geometry of the shaft elements and material selection for those elements. The manner in which stiffening elements in the shaft are positioned within the shaft and are connected or unconnected to the shaft also affect shaft stiffness. For example, in accordance with the present teachings, stiffening elements positioned within the shaft may not be physically connected to the shaft be simply sit or "float" within the shaft, minimizing the number of stiffening elements that are loaded during initial bending of the shaft and thus contribute to the overall bending stiffness of the shaft.

Various design aspects may be used for the flexible instrument shafts. The following descriptions disclose example implementations of flexible shafts used for instruments with a movable end effector component, and it should be understood that the principles described (e.g., ways of stiffening) may be adapted for shafts that do not have an end effector with a moving component. It should also be understood that the principles may be adapted to instrument aspects that include a movable wrist mechanism or other mechanism at the distal end of the instrument shaft.

Surgical instrument end effectors placed at the distal end of the flexible shaft instruments are of two general types. The first type of end effector has no moving parts. Such non-moving end effectors may include, for example, suction/irrigation tips, electrocautery hooks or blades, probes, blunt dissectors, cameras, retractors, etc. The second type of end effector has at least one moving component that is actuated under computer-assisted control. Such moving component end effectors include, for example, graspers, needle drivers, moving cautery hooks, clip appliers, shears (both non-cautery and cautery), etc.

As disclosed herein, end effector component(s) are actuated by a single compression/tension element that moves the end effector component. In such a "push/pull" design, pulling (tension) is used to move the component in one direction, and pushing (compression) is used to move the component in the opposite direction. In some implementations, the tension force is used to actuate the end effector component in the direction that requires the highest force (e.g., closing jaws). Placing the push/pull drive rod in tension may increase axial compression of the instrument shaft during actuation of the end effector. Alternative mechanisms for actuating an end effector are known and discussed in U.S. Published Application No. 2011/0071542 A1, published on Mar. 24, 2011, and incorporated herein by reference.

Design considerations for a suitable instrument shaft include bending stiffness and axial stiffness of the instrument shaft. In particular, it is desirable to maximize the axial stiffness of the shaft (i.e., to provide resistance to axial compression of the shaft and support for the end effector) while minimizing the bending stiffness of the shaft (e.g., to permit ease of access through the curved cannula and the single port to the surgical site). Maximizing axial stiffness of the shaft (i.e., maximizing resistance to axial compression of the shaft) allows more efficient transfer of force from a drive element of the shaft to the end effector and may facilitate tighter control of the end effector by minimizing undirected movement of the end effector during actuation of the drive element. Other design considerations such as materials used and their characteristics (e.g., flexural modulus, tensile strength, coefficient of friction, etc.), dimensions of elements (e.g., drive rod, stiffening rod, etc.) contained within the shaft, and placement of elements in relation to each other allow variations of and interplay between the bending stiffness and the axial stiffness of an instrument shaft in accordance with the present teachings.

FIG. 3 is a diagrammatic view of an exemplary flexible instrument 300 used with a curved cannula 116. Instrument 300 includes a proximal end force transmission mechanism 330, a distal end surgical end effector 304, and a shaft 306 that couples force transmission mechanism 330 and end effector 304. The shaft may range between 30 cm and 60 cm in length, and in one implementation, shaft 306 is about 43 cm in length. The shaft 306 may have the same axial stiffness along its length. Alternatively, the shaft may vary in stiffness along its length to accommodate different portions of a curved cannula. Examples of variations in the stiffness of the shaft are discussed in detail in U.S. Published Application No. 2011/0071542 A1, published on Mar. 24, 2011, and incorporated herein by reference.

Figure 5:
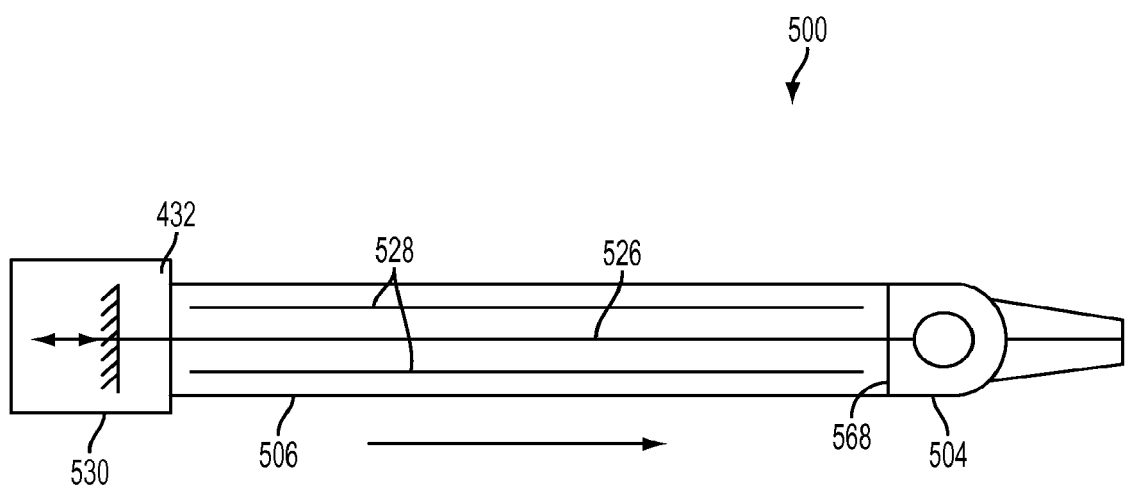
FIG. 5 is a cross-sectional side view of an exemplary push/pull instrument in accordance with the present teachings.

FIG. 5 is a cross-sectional side view of an exemplary surgical instrument that illustrates aspects of a push/pull instrument design. As shown in FIG. 5, an instrument force transmission mechanism 530 is coupled to a grip-type end effector 504 by a flexible shaft body 506. A compression/tension drive element 526 is routed through shaft body 506 and couples a movable component in end effector 504 to a component (not shown; see description of FIGS. 4A and 4B above) in transmission mechanism 530 that receives a robotic actuation force. When the drive rod 526 is actuated (i.e., placed in tension), the push/pull drive rod compresses substantially the entire shaft 506 of instrument 500. In order to offset the compression loads on the shaft 506, one or more axial stiffening rods are provided within the body of shaft 506. The stiffening rods are radially spaced from the drive rod and evenly spaced around drive rod to surround the drive rod. Each stiffening rod is positioned in the shaft, between the force transmission mechanism and the end effector of the instrument. The stiffening rods are not, however, anchored within or otherwise connected to ends of the shaft and instead float freely within the shaft. Allowing the stiffening rod(s) to float within the shaft reduces the effect such rods have on the bending stiffness of the flexible shaft. In addition, in cases where more than one stiffening rod is provided, because the stiffening rods float within the shaft, only a single stiffening rod is actuated or engages during initial bending of the drive rod or as drive rod is initially actuated. When the shaft 506 is bent, a stiffening rod along the shortest path between ends of the shaft 506 engages both ends of the shaft 506, thereby providing resistance to axial compression of the shaft 506. In such a bent shaft, there is a differential length between the paths along which the engaged stiffening rod passes and paths that other stiffening rods pass. The difference in length along these paths may be minimized by, for example, by positioning the stiffening rods closer to the center of the multi-lumen shaft 506 and drive rod 526. Such a configuration may provide greater control over the instrument and end effector.

As the shaft rolls, the stiffening rod along the shortest path of the shaft changes, changing the stiffening rod that contributes to the axial stiffness of the shaft. As the drive element (push/pull rod or drive rod) is actuated, it may be placed in tension (pulling) or compression (pushing). As the drive rod is actuated under tension, it compresses the shaft 506 and, thus, the path lengths of the stiffening rods shorten. The arrow in FIG. 5 represents the axial compression of the shaft along the longitudinal axis of the shaft during actuation of the end effector. As the path lengths shorten, additional stiffening rods are engaged to further resist axial compression of the shaft 506. During bending of the shaft, the stiffening rods float within the shaft body and do not pull against either end of the shaft of the instrument. The lack of additional forces created during bending of the shaft reduces the overall bending stiffness of the shaft. Although the presence of the stiffening rods does contribute the overall bending stiffness of the shaft, this contribution can be further minimized by controlling design aspects of the stiffening rods, such as the diameter of the stiffening rods, the material from which the rods are made, etc.

Shaft body materials have an elastic modulus (or Young's modulus) low enough to allow bending with low enough radial force to limit friction inside a curved cannula so that instrument insertion and withdrawal is not affected in a meaningful way, but its modulus of elasticity is high enough to provide good cantilever beam stiffness for a distal portion of the surgical instrument (shaft and end effector) that extends beyond the distal end of the curved cannula, to resist buckling of any portion of the shaft between the transmission mechanism and the proximal end of the cannula, and to transmit roll motion and torque along the length of the instrument shaft with adequate stiffness and precision.

For example, the bending stiffness of an instrument shaft in accordance with the present disclosure may be modeled using the bending stiffness of an outer/main tube of the shaft, the bending stiffness of the drive rod of the instrument, and the bending stiffness of stiffening rods used to provide axial strength to the instrument shaft. The bending stiffness for a drive rod or a stiffening rod ($K_{bend_{rod}}$) may be modeled using the following formula:

$$K_{bend_{rod}} = E * I \tag{1}$$

where E=flexural modulus and I=area moment of inertia of cross-section of the rod. The area moment of inertia can be calculated using the formula:

$$I_{rod} = \frac{\pi * r^4}{4} \tag{2}$$

where r=the radius of the rod. The bending stiffness and area moment of inertia of cross-section of the outer or main body tube of the shaft may be calculated in the same manner used for the rod, but accounting for the hollow cross section of the tube in the area moment of inertia using the formula:

$$I_{main\ body\ tube} = = \frac{\pi}{4} * (r_o^4 - r_i^4) \tag{3}$$

where $r_o$ is the outer radius of the outer/main tube and $r_i$ is the inner radius of the outer or main body tube. Once the bending stiffness of the drive rod and of any stiffening rods have been calculated, as well as the bending stiffness for the outer or main body tube, the bending stiffness for the instrument shaft ($K_{bend_{shaft}}$) can be modeled using the following formula:

$$K_{bend_{shaft}} = K_{bend_{main\ body\ tube}} + K_{bend_{drive\ rod}} + N * K_{bend_{stiffening\ rod}} \tag{4}$$

where $K_{bend}$ is bending stiffness and N is the number of stiffening rods contained in the shaft. Although the bending stiffness of the multilumen tube ($K_{bend_{multilumen}}$) technically contributes to the bending stiffness of the shaft, it is negligible for practical purposes and has for this reason is not listed equation (4) above. However, as one of skill in the art will understand, the selection of materials used for the multi-lumen tube may render this variable more impactful on the overall bending stiffness.

In a flexible shafted instrument in accordance with the present teachings, the goal is to identify a bending stiffness of the shaft, $K_{bend\ shaft}$, that is substantially equal to the bending stiffness of the main body tube of the shaft, $K_{bend_{main\ body\ tube}}$. That is, the bending stiffness of the stiffening rod(s) should minimally contribute to the overall bending stiffness of the shaft while maximizing the axial stiffness of the shaft. By selecting a material with a high tensile modulus (c) for the stiffening rod, the axial stiffness of the instrument shaft is increased. By selecting a small radius for the stiffening rods (significantly smaller than 0.1 cm), the area moment of inertia is very small which reduces the additional bending stiffness added by the stiffening rods. For example, the diameter range for stiffening elements made from stainless steel may range between 0.5 mm and 1.25 mm. The diameter range for stiffening elements will depend upon the particular materials selected as well as the degree of curvature of the cannula to be traversed.

As discussed above, only one stiffening rod contributes to the axial stiffness of the shaft of the surgical instrument during bending of the shaft (the stiffening rod along the shortest path in the shaft as the shaft is placed in tension or compression is loaded in a curved instrument, the other wires are floating). During bending of the shaft, the axial stiffness of the shaft is substantially equal to the sum of the axial stiffness of the outer tube and one stiffening rod when the end effector is not being actuated by the drive rod. As actuation of the end effector proceeds, the shaft is compressed shortening the path length of the remaining stiffening rods, allowing additional stiffening rods to engage and, thus, gradually increasing the axial stiffness of the shaft as the additional stiffening rods engage. Such engagement may be substantially simultaneous or it may be gradual as the additional stiffening rods are consecutively engaged. When the drive rod is fully loaded such that all stiffening rods are engaged, the axial stiffness of the shaft is equal to the sum of the outer tube axial stiffness and the total stiffness of the plurality of stiffening rods Any support tube provided within the shaft body, for example to align the stiffening rods and/or providing flush channels, also may be unanchored or free floating within the shaft so as not to contribute to the axial stiffness of the shaft. For the same reasons, such a support tube may have a length shorter than that of the axial stiffening rods such that it will not engage when the stiffening rods engage. Additionally or alternatively, the support tube may be made from materials having substantially lower axial stiffness.

The axial stiffness of the drive rod and the axial stiffness of a stiffening rod may each be determined using the following formulas:

$$K_{axial} = \frac{\varepsilon * A}{L} \quad (5)$$

and $A_{rod} = \pi * r^2$ (6)

where $K_{axial}$ is the axial stiffness, $\varepsilon$ is the tensile modulus of the material used for the drive rod or stiffening rod, $A_{rod}$ is the cross-sectional area of the drive rod or stiffening rod, L is the length of the drive rod or stiffening rod, and r is the radius of the drive rod or stiffening rod. The axial stiffness of the main body tube of the shaft may be determined using the following formulas:

$$K_{axial_{main\ body\ tube}} = \frac{\varepsilon * A}{L} \quad (7)$$

and $A_{main\ body\ tube} = \pi * (r_o^2 - r_i^2)$ (8)

where $r_o$ is the outer radius of the outer/main tube and $r_i$ is the inner radius of the outer or main body tube.

Using the axial stiffness values for the drive rod, the main body tube of the shaft, and the stiffening rod, the axial stiffness of the instrument shaft, $K_{axial_{shaft}}$ may be modeled using the following formula:

$$\frac{1}{K_{axial_{shaft}}} = \frac{1}{K_{axial_{drive\ rod}}} + \frac{1}{K_{axial_{main\ body\ tube}} + K_{axial_{stiffening\ rod}}}.$$

In the above equation, the axial stiffness of the instrument shaft is modeled for one (1) engaged stiffening rod. If additional stiffening rods are to be engaged, their axial stiffness would need to be accounted for the above equation.

Using the modeled values for the bending stiffness of the instrument shaft, $K_{bend_{shaft}}$, and the axial stiffness of the instrument shaft, $K_{axial_{shaft}}$, it is possible, through shifting variables such as materials used, size of elements, etc. to minimize the bending stiffness of the instrument shaft while providing sufficient axial strength to the instrument shaft to support the end effector during surgical use.

It is possible to vary both the axial stiffness and the bending stiffness of the shaft in accordance with the intended use of the surgical instrument. For example, in some implementations, use of a robotic surgical system permits the bending stiffness of the instrument shaft (or at least the portion of the shaft that moves within the cannula) to be substantially greater than an instrument shaft intended to be wielded manually. The robot can, in certain instances, apply forces to insert an instrument shaft through a curved cannula and control movement of that instrument, e.g., through roll of the instrument, that are substantially higher than forces that can be reasonably controlled by a human. The ability to apply greater forces via robot permits an instrument shaft to have a bending stiffness substantially higher than hand-operated instrument shaft stiffness would be for a similar but manually actuated curved cannula system. This characteristic enables the use of a curved cannula robotic surgical system in situations in which hand-operated instruments acting through curved cannulas may be marginally functional or non-functional (e.g., the hand-operated shaft stiffness is too low to enable the instrument to effectively work at the surgical site). And so, in some implementations, the instrument shaft is "tuned" (e.g., by selecting one or more particular materials and/or by various shaft constructions using the selected material(s)) to (i) make effective use of the robot's insertion and roll drive capabilities with reasonably stiff shafts while (ii) not allowing the friction between such reasonably stiff shafts and a particular cannula curve dimension to offset the robot's drive capability benefits. Thus certain instruments may have flexible shafts with a first bending stiffness and first axial stiffness for use with cannulas with one curve radius and/or inner diameter, and other instruments may have shafts of another bending stiffness and another axial stiffness for use with cannulas with another curve radius and/or inner diameter. Various permutations of the axial stiffness and the bending stiffness may be incorporated into a flexible instrument shaft, depending upon the intended use of the instrument, in accordance with the present teachings.

For example, for a particular shaft diameter and assuming cannula curve radius and cannula-shaft friction vary inversely, shaft bending stiffness for an instrument designed for use with a cannula having a relatively larger curve radius may be greater than shaft bending stiffness for an instrument designed for use with a cannula having a relatively smaller curve radius. Cannulas having specific curve angles and bend radii may be used for particular surgical procedures. For example, one cannula length, curve angle, and bend radius may be best suited for reaching from a particular incision point (e.g., at the umbilicus) towards one particular anatomical structure (e.g., the gall bladder) while another cannula length, bend angle, and/or bend radius may be best suited for reaching from the particular incision point towards a second particular anatomical structure (e.g., the appendix). And, in some implementations two cannulas each having different lengths and/or bend radii may be used. In such cases, it may be desirable to have surgical instruments with shafts of various bending stiffnesses and axial stiffnesses in order to maximize both access to the surgical site and mobility and usefulness of the end effector working through each cannula.

In various aspects, the shaft's bending stiffness (this may also be referred to as a lateral stiffness of the shaft) is in a range from about 1 lb-in$^2$ (PSI×in$^4$) to about 4 lb-in$^2$, and in one implementation the shaft's lateral stiffness is about 2.0 lb-in$^2$. With regard to the axial stiffness of the shaft, the larger the tensile or compressive force applied to the instrument via the drive rod, the greater the axial stiffness of the shaft should be to offset those applied forces. For example, in accordance with the present teachings, a drive rod may apply a force of between 2 lb. and 30 lb. to the instrument, depending upon the particular instrument end effector and clinical load on the end effector. To accommodate such forces, each stiffening rod, in accordance with the present teachings, may provide an axial stiffness of between about 500 lb/in to about 800 lb/in (or, said another way, each stiffening rod may resist between about 500 lb/in to about 800 lb/in of axial compression of the shaft). Thus, as the compressive force applied by the drive rod increases, the number of stiffening rods that engage increases, effectively resisting axial compression of the shaft caused by the actuation.

Figure 6A:
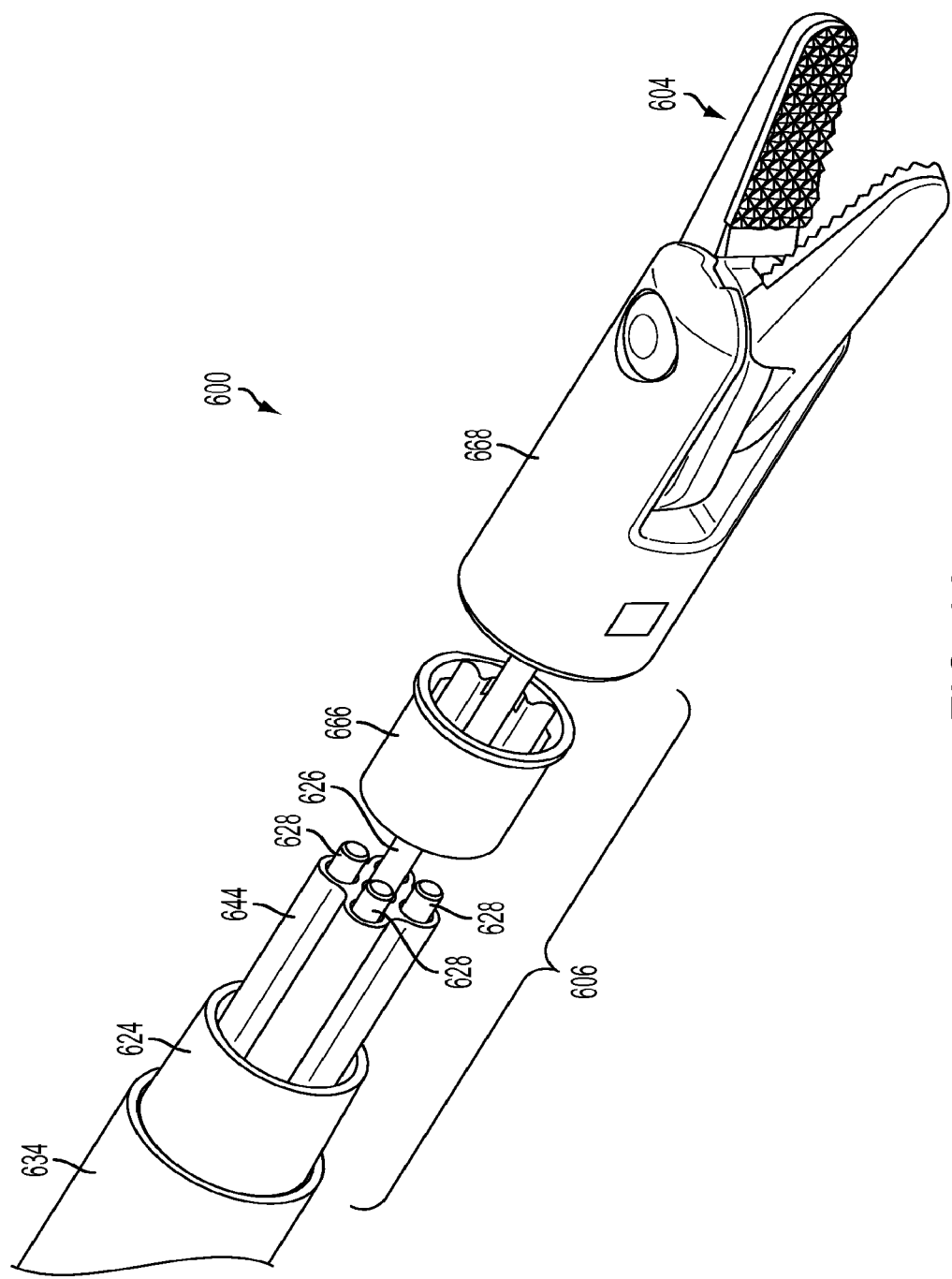
FIG. 6A is a perspective view of an exemplary embodiment of a distal end of a flexible surgical instrument according to the present teachings.
Figure 6B:
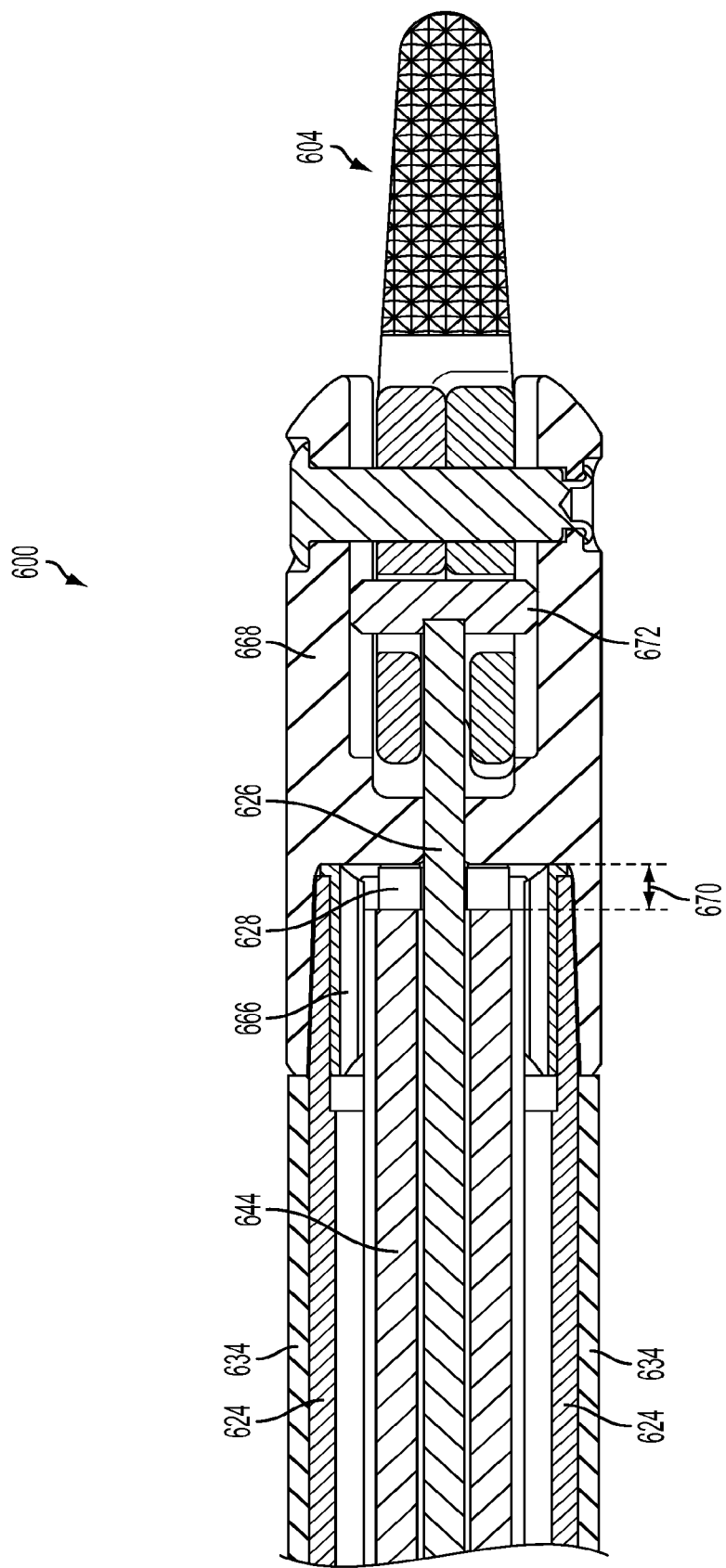
FIG. 6B is a cross-sectional side view of the distal end of the flexible surgical instrument of FIG. 6A.
Figure 6C:
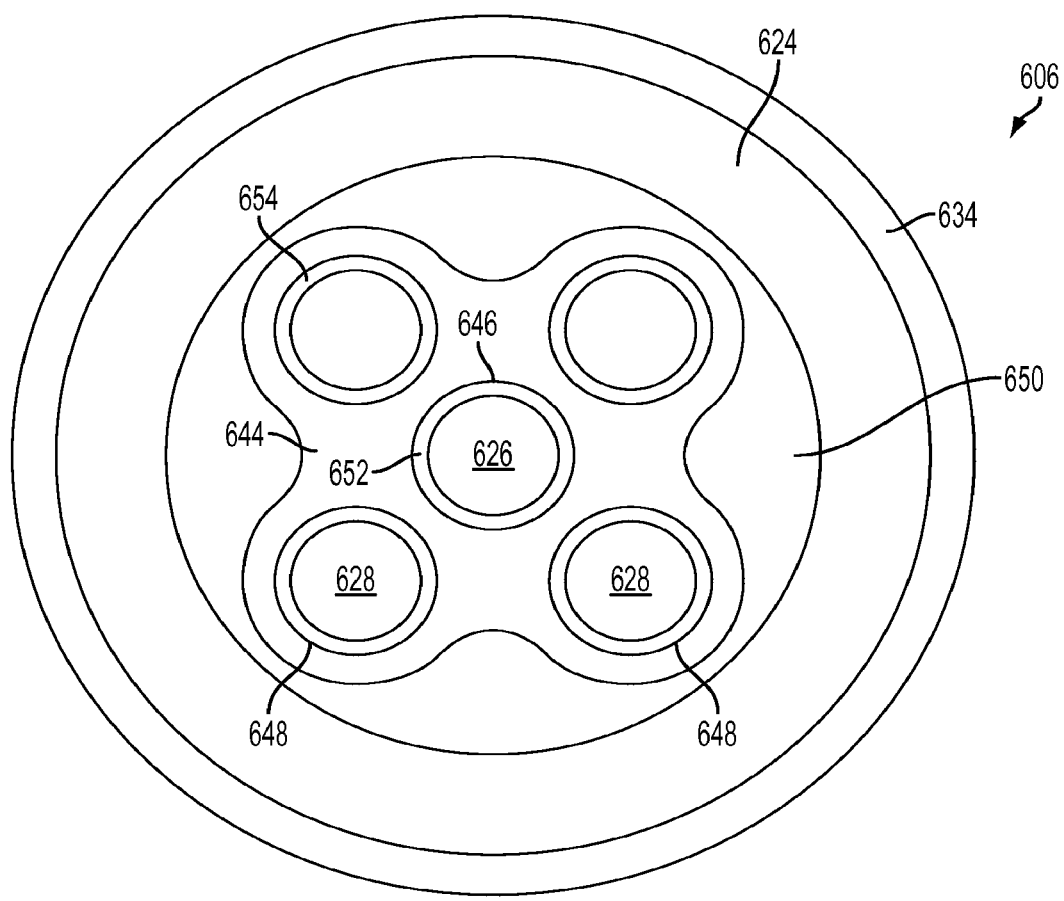
FIG. 6C is a radial cross section of the shaft of the flexible surgical instrument of FIG. 6A.

Examples of instrument shafts in accordance with the present teachings are described in reference to FIGS. 6A-6E below. FIG. 6A is a perspective view of a distal end of a flexible surgical instrument in accordance with the present teachings. FIG. 6B is a cross-sectional side view of the distal end of the flexible surgical instrument of FIG. 6A and FIG. 6C is a radial cross section of the shaft of the flexible surgical instrument of FIG. 6A.

As shown in FIG. 6A, a surgical instrument 600 includes a flexible shaft 606. Shaft 606 includes an outer or main body tube that forms a shaft body 624. Through this description, the terms "outer body tube" and "main body tube" are used interchangeably. Shaft body 624 provides axial and torsional stiffness to shaft 606. The inner and outer diameters of shaft body 624, as well as the material used for shaft body 624, are selected to provide a desired bending stiffness of the shaft body 624. Shaft body 624 may be made, for example, of a high stiffness plastic. In one exemplary embodiment, shaft body 624 is made of polyether ether ketone (PEEK). Other suitable materials such as an aliphatic polyamide (nylon) which can be glass or carbon filled, polyetherimide (PEI) which can be glass or carbon filled, thermoplastic elastomers (TPE) such as polyether block amide (PEBA) which can be reinforced, and epoxy and carbon fiber and epoxy and glass fiber pultruded tubes may be used for shaft body 624. Materials may be selected such that the shaft body 624 is autoclavable or is disposable. Shaft body 624 may have an outer diameter, for example, of about 5 mm, and an inner diameter of about 3.5 mm. Alternatively, depending upon the size of the curved cannula provided, and the number of cannulas to be used through the single port access, shaft outer diameters of 3 mm or 8 mm may be used, with respective inner diameters of 1 mm to 7 mm.

As illustrated in FIG. 6A, shaft body 624 may include an outer skin or outer coating 634. Outer skin or coating 634 surrounds shaft body 624 and reduces friction between shaft 606 and an interior of a curved cannula as shaft 606 slides within the curved cannula. A heat shrink material such as ethylene tetrafluoroethylene (ETFE) may be used to form outer skin 634. Alternatively, other suitable materials may be used. The outer skin or outer coating 634 is generally a thin coating, for example, a coating of about 0.005 inches.

Within shaft body 624, a multi-lumen tube 644 provides support and alignment for a push/pull drive rod 626 of the surgical instrument 600. Multi-lumen tube 644 includes a central lumen 646 through which push/pull drive rod 626 extends. Multi-lumen tube 644 may include several lumens 648 radially spaced from central lumen 646. Multi-lumen tube 644 may be made from a soft flexible plastic such as a low friction Teflon or a fluorinated polymer. In one exemplary embodiment, multi-lumen tube 644 comprises a fluorinated ethylene propylene (FEP) extrusion. FEP provides a low-friction surface against which elements within the lumens slide. Alternatively, other suitable materials such as ethylene tetrafluoroethylene (ETFE) or polytetrafluoroethylene (PTFE) may be used. Multi-lumen tube 644 is not anchored within shaft body 624, and multi-lumen tube 644 is shorter in length than shaft body 624, such that multi-lumen tube 644 is moveable or "floats" within shaft body 624.

As illustrated in FIGS. 6A and 6C, multi-lumen tube 644 may have a lobed cross section. Although illustrated in the exemplary embodiment of FIGS. 6A and 6C as having four semi-cylindrical lobes (semi-circular in cross section), it should be understood that the "lobes" are not so limited in shape and may have any suitable shape, such as rectangular, triangular, square, etc., as illustrated in FIGS. 6F-6I. The number of lobes may be selected to correspond to the number of stiffening rods, although it is possible that certain structures may have lobes configured to support more than one stiffening rod. Additionally, the shapes of the lobes may have corners, straight edges, or rounded edges, and such design features may be selected based in part on the desired bending stiffness of the shaft. Certain shapes may be desirable for providing additional space within shaft body 624 to pass additional elements through the shaft, such as wires, or to provide a fluid flush path. Additionally or alternatively, certain shapes may provide for different positioning and/or spacing of the stiffening rods 628 relative to the drive rod 626.

As illustrated in FIGS. 6A-6E, push/pull drive rod 626 extends through the center of multi-lumen tube 644 and is slidably moveable within central lumen 646 of multi-lumen tube 646. In such a "push/pull" design, pulling (tension) is used to move the component in one direction, and pushing (compression) is used to move the component in the opposite direction. In some implementations, the tension force is used to actuate the end effector component in the direction that requires the highest force (e.g., closing jaws). Push/pull drive rod 626 may be made from any suitable material, such as for example, stainless steel. Additional suitable materials include, for example, aluminum, carbon fiber, and NITINOL. The push/pull drive rod 626 must be made of a material and of a size sufficient to withstand the tensile and compressive forces applied during actuation of the end effector. Generally, the drive rod may be subjected to a load of between about 2 lb. and 30 lb. during tension and/or compression. In accordance with the present teachings, a solid stainless steel drive rod may have an outer diameter of between 0.5 mm and 1.25 mm. In one exemplary embodiment, push/pull drive rod 626 is a solid rod, made of 304 stainless steel (stainless spring steel), with an outer diameter of 0.032 inches. Diameters will vary depending upon the material selection.

As shown in FIGS. 6A-6E, one or more stiffening rods 628 are provided to increase axial stiffness of shaft 606. The number, size, and composition of stiffening rods 628 may be selected to provide a desired axial stiffness to shaft 606 while minimizing the impact on the bending stiffness of shaft 606 (i.e., without increasing the bending stiffness). Like multi-lumen tube 644, stiffening rods 628 are not anchored within shaft body 624 and are free to move or float within shaft body 624. Because stiffening rods 628 float within multi-lumen tube 644 and shaft body 624, only a single stiffening wire contributes to the bending stiffness of the instrument shaft 606. When the shaft 606 is bent, a stiffening rod along the shortest path between ends of the shaft 606 is the stiffening rod that is engages and increases the axial stiffness of the shaft 606. As the shaft rolls, the stiffening rod along the shortest path of the shaft changes, changing the stiffening rod that contributes to the axial stiffness of the shaft. During bending of the shaft, multi-lumen tube 644 continues to float within shaft body 624 and is shorter than stiffening rods 628 such that it does not engage and contribute to the axial stiffness of the shaft 606.

During actuation of the drive rod 626, the push/pull drive rod compresses substantially the entire shaft 606 until a first one of the stiffening rods 628 engages. As additional force is applied via drive rod 626, the shaft 606 continues to compress, shortening the paths of the stiffening rods within shaft 606. This allows additional ones of the stiffening rods to be engaged to resist axial compression of the shaft 606.

As illustrated in the exemplary embodiment of FIGS. 6A-6C, four stiffening rods 628 may be radially spaced from push/pull drive rod 626 and evenly spaced from each other to surround push/pull drive rod 626. The distance the stiffening rods 628 are spaced from push/pull rod 626 may be varied based on the materials used for the drive rod and stiffening rods and the dimensions of each. In some cases, increasing distance between the push/pull drive rod 626 and stiffening rods 628 may translate to a slack feel, a slip, or lack of responsiveness in the instrument. Moving the stiffening rods closer to the push/pull drive rod 626 and the center of the instrument shaft minimizes the differential length between the stiffening rods during bending of the instrument shaft and may improve responsiveness of the instrument (end effector) during use.

In one exemplary embodiment, the stiffening rods 628 may be positioned substantially immediately adjacent to the drive rod or drive rod channel in the multi-lumen tube 644. As noted above, this reduces the path length change during actuation of the end effector and more effectively transfers force from the drive rod 626 to the end effector, thereby offering additional control over movement of the end effector.

Figure 9A:
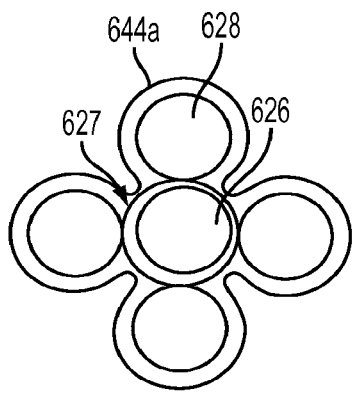
FIGS. 9A-9C are radial cross-sectional views of alternative embodiments for positioning the stiffening rods substantially immediately adjacent to the drive rod.
Figure 9B:
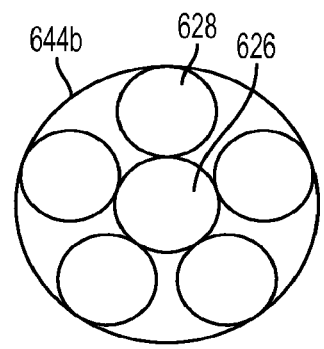
Figure 9C:
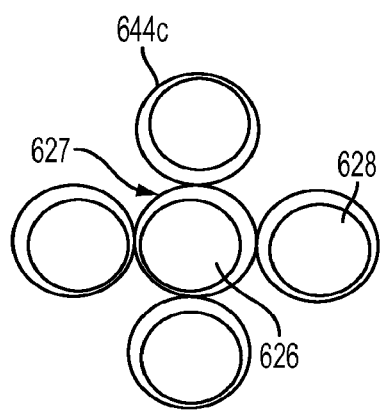

Exemplary configurations for positioning the stiffening rods 628 substantially immediately adjacent to the drive rod 626 are shown in FIGS. 9A-9C. As shown in FIG. 9A, a thin sheath 627 may surround drive rod 626 to facilitate sliding of drive rod 626 relative to stiffening rods 628, which are shown in sliding contact with sheath 627 and substantially immediately adjacent to drive rod 626. Stiffening rods 628 may be positioned within a second sheath or multi-lobed tube 644*a* to hold the stiffening rods 628 in position relative to drive rod 626. FIG. 9B illustrates an exemplary embodiment in which drive rod 626 and stiffening rods 628 are in sliding contact with one another. A sheath 644*b* may hold stiffening rods 628 in position relative to drive rod 626 while permitting sufficient space to allow relative movement between drive rod 626 and stiffening rods 628. In FIG. 9C, drive rod 626 is positioned within a sheath or lumen 627 and each stiffening rod 628 is positioned within a sheath 644*c*, with sheaths 644*c* positioned in contact with sheath 627 to place stiffening rods 628 substantially immediately adjacent drive rod 626. Sheaths 627 and 644*c* may be desirable for permitting relative movement between drive rod 626 and stiffening rods 628 and/or for providing a fluid flush path. Other embodiments in which the stiffening rods 628 are positioned substantially immediately adjacent to drive rod 626 will be understood from the present teachings and examples.

Each stiffening rod 628 passes through a respective lumen 648 of multi-lumen tube 644. Although the exemplary embodiment of FIGS. 6A-6C discloses four stiffening rods 628, it should be understood that more or less than four stiffening rods may be used. As discussed above, during bending of shaft 606, only a single stiffening rod contributes to the axial stiffness of the shaft, the stiffening rod that is along a shortest path between ends of the shaft. In accordance with one exemplary embodiment, the stiffening rods each may have a diameter equal to a diameter of push/pull drive rod 626. In addition, each stiffening rod may be made of the same material as push/pull drive rod 626, such as stainless steel 304. Other suitable materials such as aluminum, nitinol, or materials commonly used for spring elements may be used.

Stiffening rods 628 need not have a circular cross-sectional shape, and indeed may have any other suitable cross-sectional shapes, such as for example, a square or triangular shape. Additionally or alternatively, each stiffening rod 628 may comprise a single rod or a plurality or bundle of rods.

In an exemplary embodiment in which more than four stiffening rods are used, a plurality of stiffening rods sufficient to substantially form a circle or perimeter around push/pull drive element may be used. Additionally or alternatively, in place of stiffening rods which surround push/pull drive rod 626, a single tube may be used to surround push/pull drive rod 626 and increase the axial stiffness of the instrument shaft 606. Examples of tubular elements that may be used to increase axial stiffness of the instrument shaft 606 include a coil pipe, a hypotube, a helical hollow strand (HHS® Tube), a laser cut tube (examples of which are disclosed in U.S. Patent Application Publication No. 2012/0123395 A1, published on May 17, 2012, the contents of which are incorporated herein by reference), a braided tube, a torque tube (examples of which are disclosed in U.S. Patent Application Publication No. 2012/0215220 A1, published on Aug. 23, 2012, the contents of which are incorporated herein by reference), and other tubular elements having suitable stiffness. While use of a larger number of stiffening rods, or use of a tubular element to surround the drive rod may increase axial stiffness of the instrument and potentially improve instrument responsiveness, this must be balanced against the increase in bending stiffness contributed by each additional stiffening rod.

FIGS. 6A and 6B show that a distal end of multi-lumen tube 644 terminates in a distal multi-lumen end cap 666. As shown in FIG. 6B, distal end cap 666 fits inside the distal end of shaft body 624 and push/pull drive rod 626 extends through distal end cap 666 into an end effector clevis 668. Both distal end cap 666 and clevis 668 may be made, for example, of a glass-filled plastic. As illustrated in FIG. 6B, multi-lumen tube 644 does not completely fill the distal end cap 666. Instead, axial stiffening rods extend out of multi-lumen tube 644 and abut the inner surface of the distal end cap 666, creating a space 670 within end cap 666 between the distal end of multi-lumen tube 644 and the inner surface of the end cap 666.

A push/pull drive rod end effector connector 672 couples with the movable component of the end effector 604. End effector clevis 668 fits over the end of shaft body 624 and may be swaged to shaft body 624. In some embodiments, a silicone seal (not shown) is provided between the end cap 666 and the clevis 668 or between the clevis 668 and the end effector 604 to minimize leakage between the drive rod 626 and the end effector 604.

Figure 10:
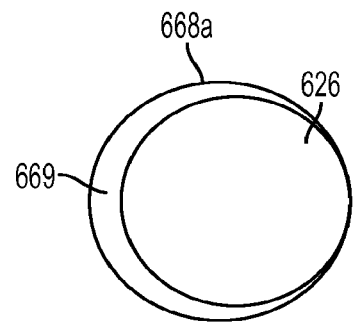
FIG. 10 is a radial cross-sectional view of a drive rod and clevis illustrating a gap between a drive rod and a clevis of an instrument shaft that controls leakage in the instrument shaft in accordance with the present teachings.

In another exemplary embodiment, a seal is not provided between the end cap 666 and the clevis 668. Instead, potential leakage between the drive rod 626 and the end effector 604 is controlled by minimizing a gap between the drive rod 626 and a passage 668*a* in clevis 668 through which the drive rod 626 passes. As illustrated in FIG. 10, the gap 669 is the difference in diameters between the drive rod 626 and the passage 668*a* in the clevis 668. The use of very small tolerances creates the small gap 669 that permits a controlled leakage rate, for example, a leakage rate of less than 25 cc/min of air. The gap 669 between the drive rod 626 and the passage 668*a* within the clevis 668 is between about 0.0000 and 0.0011 inches. A length of the gap 669 (or length of the seal (i.e., length of the passage 668*a* in the clevis 668 through which the drive rod 626 passes)) is about 0.050 inches. Elimination of a seal reduces manufacturing steps. In addition, use of a silicone seal, for example, creates the potential for the seal to be damaged or wear out and require replacement. Further, by managing the size of the gap 669 and the type of material used for the clevis 668 (e.g., a hydrophobic material) it is possible to minimize potential leakage around the drive rod 626 and clevis 668 to a rate lower than that permitted by a silicone seal. Although discussed herein with regard to an instrument shaft containing stiffening rods and other elements, it should be understood that this method of sealing using a gap between the drive rod and the passage in the rigid material forming the clevis may be used for any instrument that utilizes a push/pull drive rod as discussed herein.

Figure 6D:
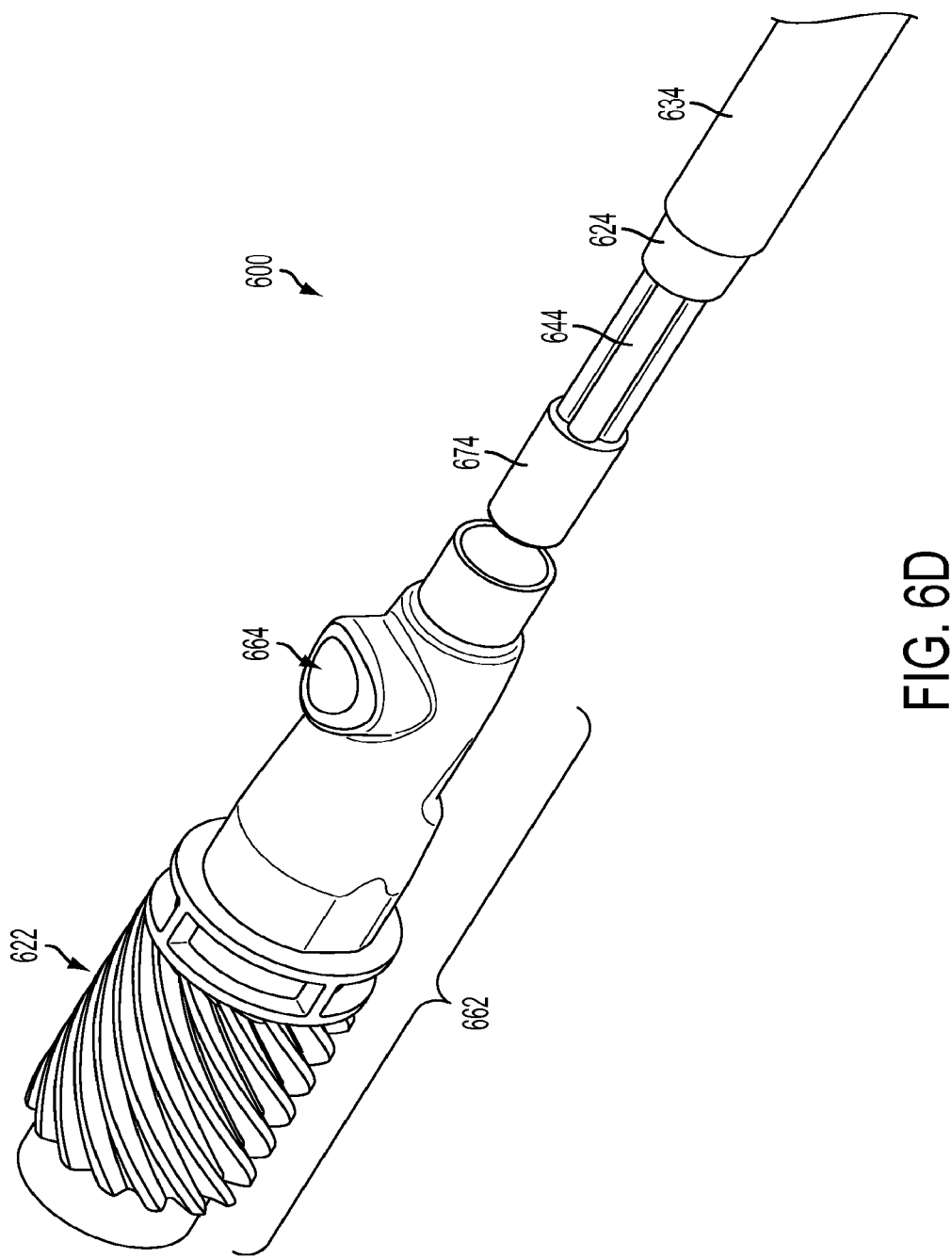
FIG. 6D is a perspective view of an exemplary embodiment of a proximal end of a flexible surgical instrument according to the present teachings.
Figure 6E:
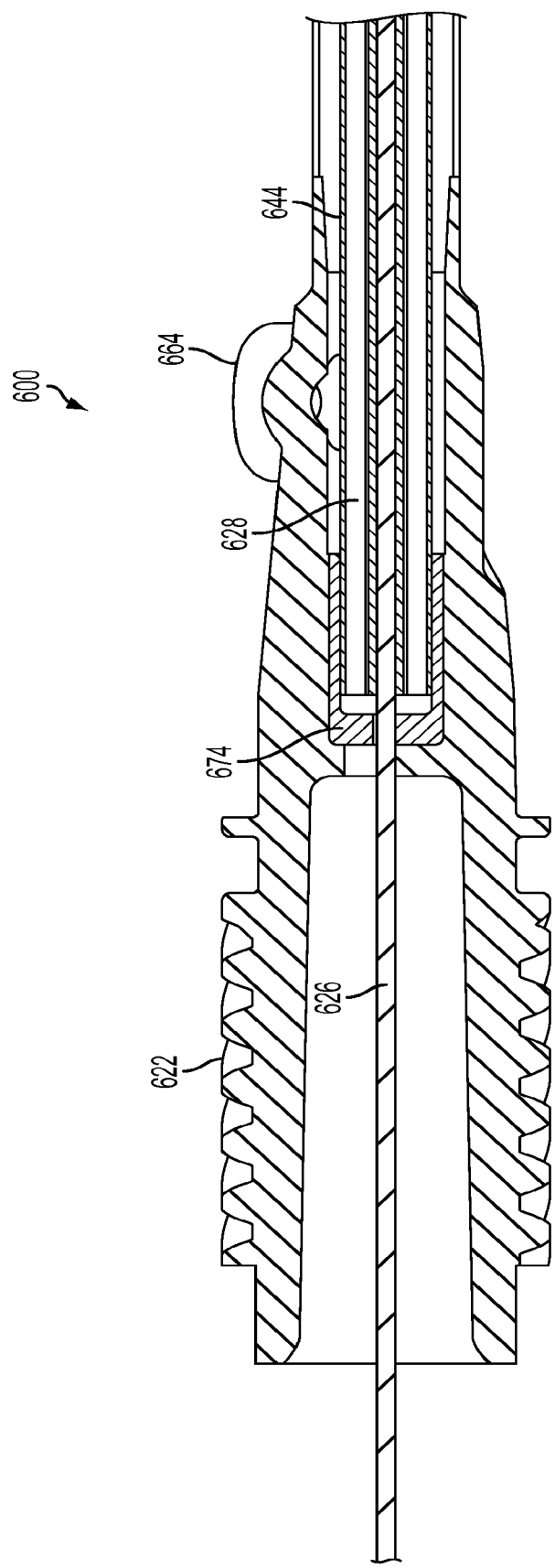
FIG. 6E is a cross-sectional side view of the proximal end of the flexible surgical instrument of FIG. 6D.
Figure 6F:
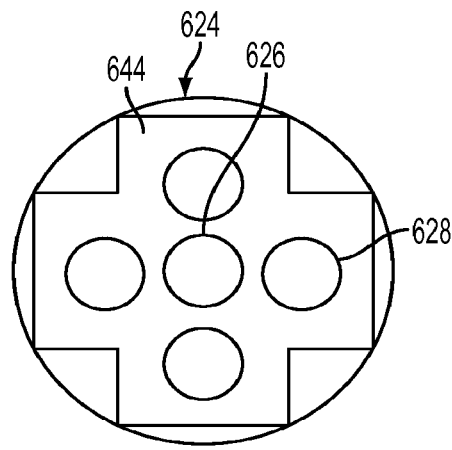
FIGS. 6F-6I are radial cross-sectional views of alternative embodiments of a distal portion of a shaft of a flexible surgical instrument in accordance with the present teachings.
Figure 6G:
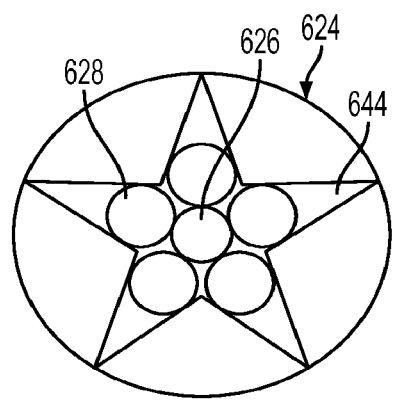
Figure 6H:
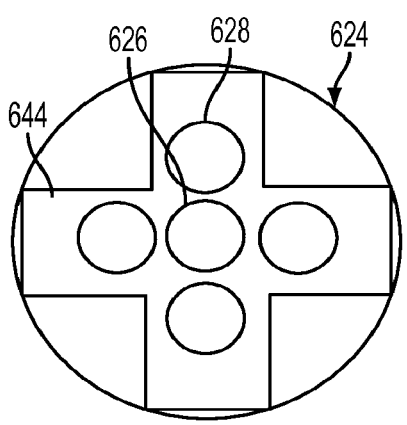
Figure 6I:
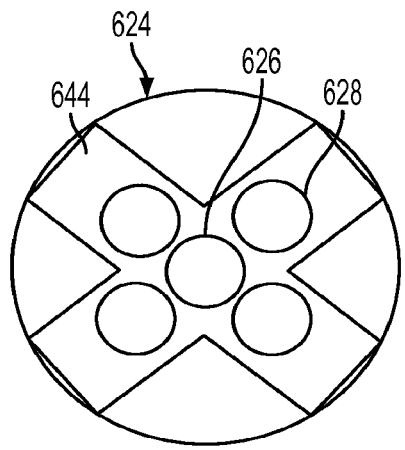

FIG. 6D is a perspective view of an exemplary embodiment of a proximal end of a flexible surgical instrument according to the present teachings. FIG. 6E is a cross-sectional side view of the proximal end of the flexible surgical instrument of FIG. 6D.

Figure 7:
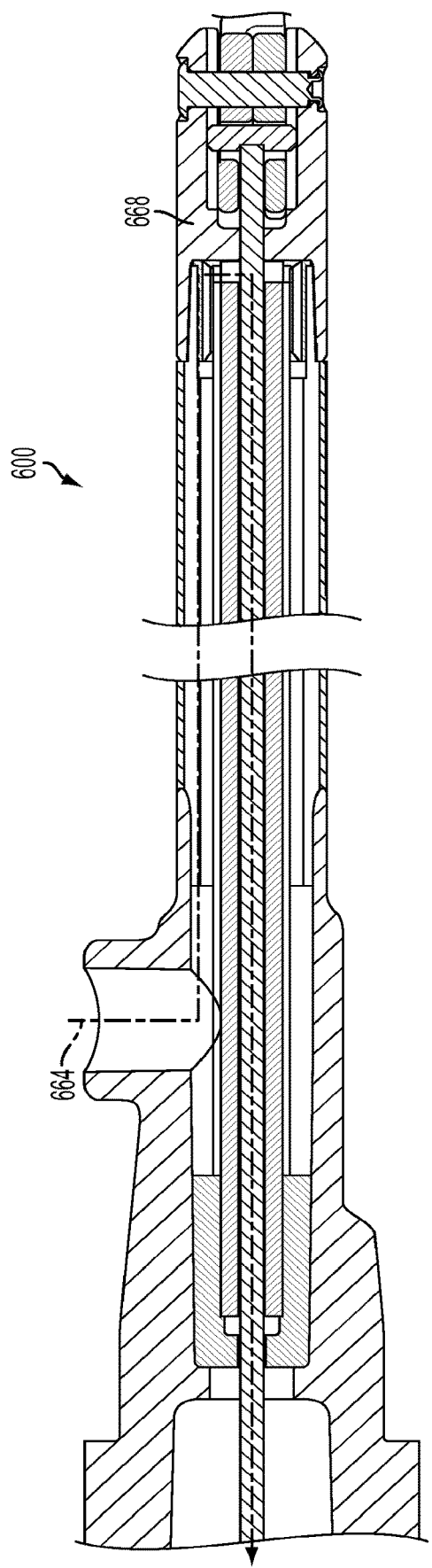
FIG. 7 is a cross-sectional side view of an exemplary shaft of a flexible surgical instrument illustrating a flush path a shaft of the instrument in accordance with the present teachings.

As shown in FIG. 6D, the proximal end of multi-lumen tube 644 terminates in a proximal end cap 674. Proximal end cap 674 fits inside a proximal end assembly 662 of instrument 610. As illustrated in FIGS. 6D and 7, drive rod 626 extends from the transmission mechanism 430 (see FIG. 4B) through roll gear 622 and proximal end assembly 662 into the proximal end of shaft 606. Proximal end cap 674 fits around drive rod 626, and is received in proximal end assembly 662 with the proximal end of shaft 606. Proximal end assembly may include a roll gear 622 and a fluid flush entry port 664. Roll gear 622 can be made out of any stiff material, suitable materials include PEEK (glass filled and non-glass filled) and stainless steel. The flush entry port is part of roll gear 622 and matches a luer fitting, the standard flush port used in a hospital setting.

As discussed above with respect to FIG. 4B, roll gear 622 forms a part of the transmission mechanism (not shown) of the surgical instrument 600. Roll gear 622 is connected to a proximal end of a shaft 606 of instrument 600. As shown, a flush fluid entry port 664 is provided at the proximal end of the instrument shaft. Fluid flush port 664 may be part of the assembly that couples the outer or main body tube of shaft 606 to the roll gear 622. Roll gear 622 is coupled (e.g., laser welded) to a stainless steel adaptor forming proximal end assembly 662, which is swaged over the proximal end of shaft body 624. Alternatively, roll gear 622 may be coupled (e.g., laser welded or glued) directly to proximal end of shaft body 624.

As shown in FIG. 6C, a space between the multi-lumen tube 644 and the inner diameter of the shaft body 624 forms an inlet flush path 650. As illustrated in FIGS. 6D, 6E, and 7, a fluid flush entry port 664 in an outer surface of a proximal end of a proximal end assembly of the surgical instrument 600 provides an entry pathway for fluid into the shaft body 624 of instrument 600. As shown by the dotted line in FIG. 7, a flush fluid entering the fluid flush entry port 664 passes around and between multi-lumen tube 644 and inner diameter of shaft body 624 as the fluid moves from a proximal end of the instrument shaft 606 toward a distal end of the instrument shaft. As the flush fluid exits the inlet flush path 650 at the distal end of multi-lumen tube 644, the flush fluid passes into space 670 between multi-lumen tube 644 and inner surface of distal end cap 666 and is redirected back into the instrument shaft by the inner surface of distal end cap 666.

As discussed above, each of the push/pull drive rod 626 and stiffening rods 628 passes through a respective lumen 646, 648 in multi-lumen tube 644. The lumens 646, 648 have a diameter larger than that of the respective rods (drive rod 626, axial stiffening rods 628) contained therein to allow clearance and movement between the rods and the multi-lumen tube 644. The space between the drive rod 626 and a wall of the central lumen 646 forms an exit flush path 652 through which fluid flows, from a distal end of the multi-lumen tube to a proximal end of the multi-lumen tube. Similarly, the space between each stiffening rod 628 and wall of a respective lumen 648 forms an exit flush path 654 through which fluid flows, from a distal end of the multi-lumen tube to a proximal end of the multi-lumen tube.

As the flush fluid exits the inlet flush path 650 at the distal end of multi-lumen tube 644, the flush fluid passes into space 670 between multi-lumen tube 644 and inner surface of distal end cap 666 and is redirected into exit fluid flush paths 652, 654 in the multi-lumen tube 644. As the fluid exits fluid flush paths 652, 654 and multi-lumen tube 644, it then passes through proximal end cap 674 and exits the proximal end of instrument 600. This fluid flow path, encompassing fluid flush entry port 664, inlet fluid flow path 650, and exit fluid flow paths 652, 654, provides a pathway for cleaning the shaft 606 of surgical instrument 600.

In accordance with the present teachings and as embodied in FIGS. 8A-8D, the instrument shaft construction disclosed herein, including shaft stiffening techniques, may be utilized with various electrosurgical treatment instruments. Electrosurgical instruments generally use high-frequency alternating current to perform a procedure on tissue of an organism, e.g., a human patient, using heat produced by electrical energy (e.g. cautery energy) applied to the tissue. Such instruments include monopolar instruments or bipolar instruments. Monopolar instruments typically deliver electrical energy through a single source electrode. A return, or sink, electrode returns electrical energy back to an energy generator disposed externally to the patient. Bipolar instruments typically deliver electrical energy through two electrodes (e.g., source and sink electrodes), typically two jaws of the end effector of the electrosurgical instrument, separately, and the return path for the current is from one pole through the other pole. Additional information on the structure and operation of electrosurgical instruments may be found, for example, in U.S. Patent Application Publication No. 2012/0215220 A1, published Aug. 23, 2012, and U.S. Patent Application Publication No. 2007/0123855, published May 31, 2007, the contents of each of which are incorporated herein by reference.

Figure 8A:
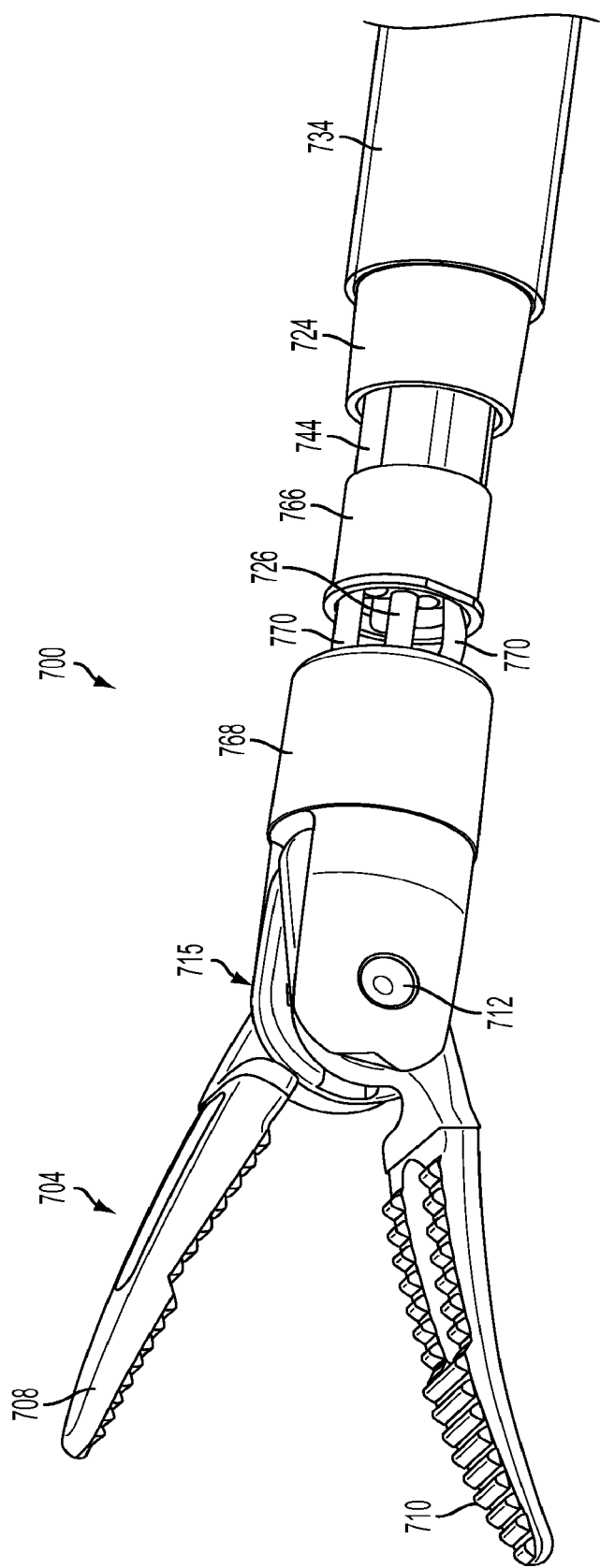
FIG. 8A is a perspective view of an exemplary embodiment of a distal end of a bipolar surgical instrument according to the present teachings.
Figure 8B:
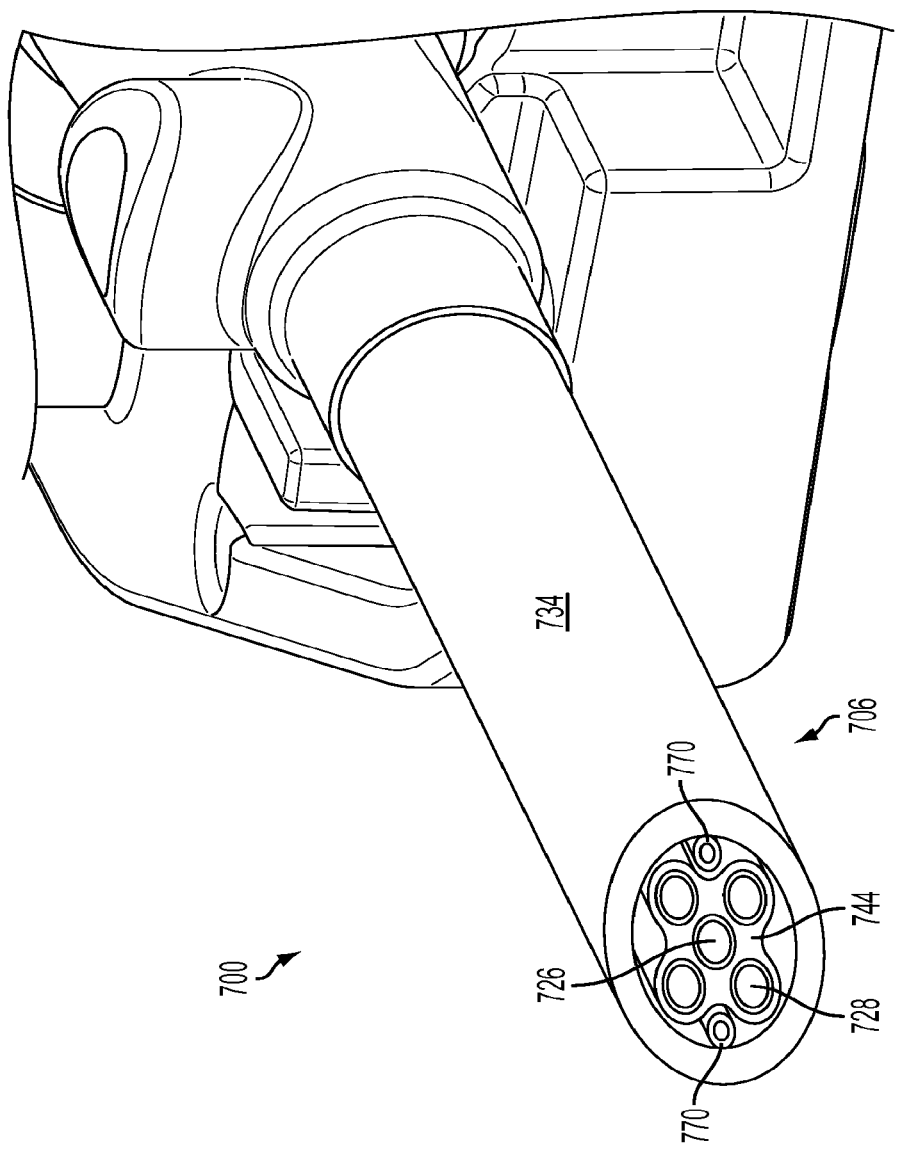
FIG. 8B is a perspective cross-sectional view of an exemplary embodiment of a proximal end of a bipolar surgical instrument according to the present teachings.
Figure 8C:
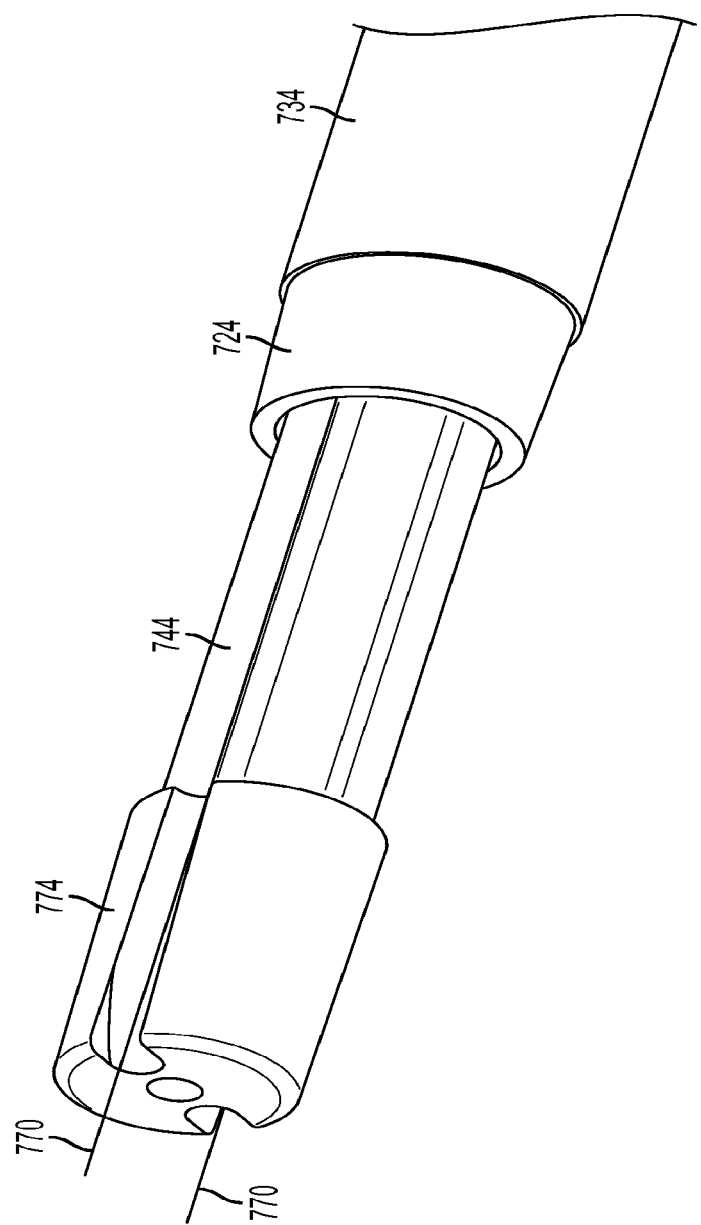
FIG. 8C is a perspective view of a proximal end of a shaft portion of a bipolar surgical instrument according to the present teachings.
Figure 8D:
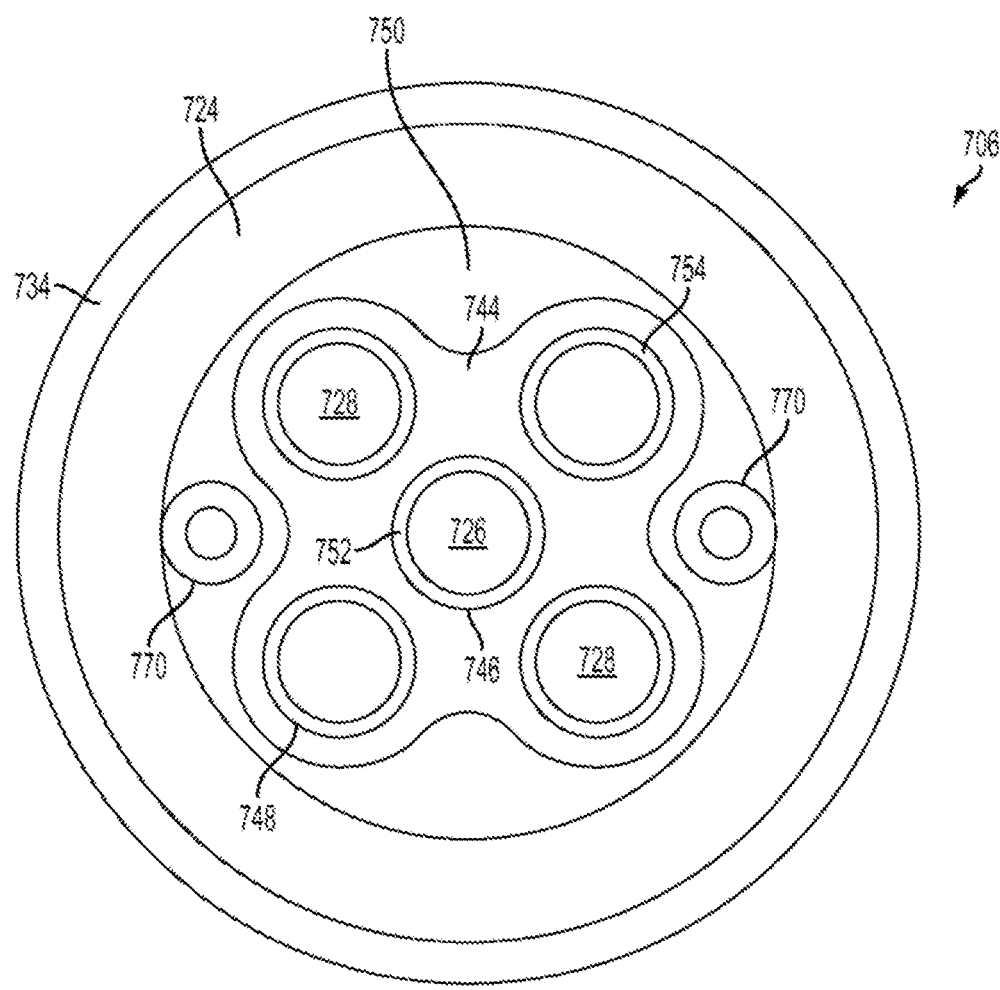
FIG. 8D is a radial cross section of the shaft of the bipolar surgical instrument of FIGS. 8A-8C.

FIG. 8A is a perspective view of an exemplary embodiment of a distal end of a bipolar surgical instrument according to the present teachings. FIG. 8B is a perspective view of an exemplary embodiment of a proximal end of a bipolar surgical instrument according to the present teachings. FIG. 8C is a perspective view of a proximal end of a shaft portion of a bipolar surgical instrument according to the present teachings. And FIG. 8D is a radial cross section of the shaft of the bipolar surgical instrument of FIGS. 8A-8C.

As illustrated in FIGS. 8A-8D, a bipolar surgical instrument 700 includes a distal end effector 704, a flexible shaft 706, and a proximal end including a force transmission mechanism 730. The bipolar distal end effector 704 can be a scalpel, blade, hook, spatula, probe, needle point, dissectors, movable jaws (e.g., clamp), and any other type of surgical end effector equipment configured to manipulate and/or cauterize tissue and the like. The particular distal end effector 704 shown in FIG. 8A is a grasper, which comprises a pair of jaws 708 and 710. In this case, one of the jaws is connected to a positive electrode and the other is connected to a negative electrode. The jaws 708 and 710 can be manipulated by actuating a push/pull drive rod 726. The jaws 708 and 710 are fastened together through a bolt 712 but separated by an insulating septum 715. When the jaws 708 and 710 are open, no electric pathway exists between them. When the jaws engage a tissue or a vessel, an electric current flows from one jaw to another, passing through the tissue or the vessel, sealing or cutting it.

As shown in FIG. 8A, shaft 706 includes an outer or main body tube that forms a shaft body 724. Shaft body 724 may include an outer skin or outer coating 734. Outer skin or coating 734 surrounds shaft body 724 and reduces friction between shaft 706 and an interior of a curved cannula as shaft 706 slides within the curved cannula. A heat shrink material such as ethylene tetrafluoroethylene (ETFE) may be used to form outer skin 734. Alternatively, other suitable materials may be used.

Within shaft body 724, a multi-lumen tube 744 provides support and alignment for a push/pull drive rod 726 of the bipolar surgical instrument 700. Multi-lumen tube 744 includes a central lumen 746 through which push/pull drive rod 726 extends. Multi-lumen tube 744 may include several lumens 748 radially spaced from central lumen 746. Multi-lumen tube 744 may be a fluorinated ethylene propylene (FEP) extrusion. FEP provides a low-friction surface against which elements within the lumens slide. Alternatively, other suitable materials may be used. Multi-lumen tube 744 is not anchored within shaft body 724, and multi-lumen tube 744 is shorter in length than shaft body 724, such that multi-lumen tube 744 is moveable or "floats" within shaft body 724.

As illustrated in FIGS. 8A-8D, push/pull drive rod 726 extends through the center of multi-lumen tube 744 and is slidably moveable within central lumen 746 of multi-lumen tube 746. In such a "push/pull" design, pulling (tension) is used to move the component in one direction, and pushing (compression) is used to move the component in the opposite direction. Push/pull drive rod 726 may be made from any suitable material, such as for example, stainless steel. Additional suitable materials include, for example, aluminum. The push/pull drive rod 726 must be made of a material and of a size sufficient to withstand the tensile and compressive forces applied during actuation of the end effector.

As shown in FIGS. 8A-8D, one or more stiffening rods 728 are provided to increase axial stiffness of shaft 706. The number, size, and composition of stiffening rods 728 may be selected to provide a desired axial stiffness to shaft 706 while minimizing the impact on the bending stiffness of shaft 706 (i.e., without increasing the bending stiffness). Like multi-lumen tube 744, stiffening rods 728 are not anchored within shaft body 724 and are free to move or float within shaft body 724. As discussed above with regard to FIGS. 6A-6E, only a single stiffening wire contributes to the initial axial stiffness of the instrument shaft 706.

As illustrated in the exemplary embodiment of FIGS. 8A-8D, four stiffening rods 728 may be radially spaced from push/pull drive rod 726 and evenly spaced from each other to surround push/pull drive rod 726. The distance the stiffening rods 728 are spaced from push/pull rod 726 may be varied based on the materials used for the drive rod and stiffening rods and the dimensions of each. In some cases, increasing distance between the push/pull drive rod 726 and stiffening rods 728 may translate to a slack feel, a slip, or lack of responsiveness in the instrument. In one exemplary embodiment, the stiffening rods 728 are positioned immediately adjacent to push/pull rod 726. As used herein, immediately adjacent includes the push/pull drive rod 726 and one or more stiffening rods 728 being in contact or separated by only a thin sheath or other material used to position and hold the push/pull rod 726 and one or more stiffening rods 728 relative to one another. In accordance with one exemplary embodiment, a stiffening rod 728 and a drive rod 726 positioned a distance of 0.0063 inches away from one another are considered to be positioned "immediately adjacent" to one another. Moving the stiffening rods closer to the push/pull drive rod 726 and the center of the instrument shaft minimizes the differential length between the stiffening rods during bending of the instrument shaft, thus transferring rod force to the end effector more effectively, and may improve responsiveness of the instrument (end effector) during use (e.g., provide more control over movement).

As discussed above with respect to the exemplary embodiment of FIGS. 6A-6C, each stiffening rod 728 may be made of the same material as push/pull drive rod 726, such as stainless steel 304. Alternatively, for a monopolar or a bipolar surgical instrument, it may be advantageous to use nonconductive materials for the axial stiffening rods 728 to eliminate the possibility of capacitive coupling. Capacitive coupling occurs when energy is transferred from an electrode (conductor) through insulation and into other electrically isolated but conductive adjacent materials, such as other instruments, cannulas, or patient tissue. Although capacitive coupling is less of a risk with bipolar electrosurgical instruments than with monopolar instruments, use of nonconductive materials in the shaft 706 of the instrument can further reduce and/or eliminate this risk. Examples of suitable nonconductive materials to be used with the stiffening rods include ceramics, zirconium, glass, fiberglass, and plastic. In addition, due to the structure surrounding the axial stiffening rods 728, being positioned within multi-lumen tube 744 and being contained therein by proximal and distal end caps, 774 and 766, it is possible to use brittle nonconductive materials for the stiffening rods 728. Should a stiffening rod 728 made from a brittle material fracture, it will still be capable of providing axial strength to shaft 706 in the shaft structure disclosed herein. In particular, the stiffening rod 728 can be sized to minimize the risk of fracture. Should fracture occur, the material would be contained within the main tube 724, and in some cases within multi-lumen tube 744.

Stiffening rods 728 need not have a circular cross-sectional shape, and indeed may have any other suitable cross-sectional shapes, such as for example, a square or triangular shape. Additionally or alternatively, each stiffening rod 728 may comprise a single rod or a plurality or bundle of rods. In an exemplary embodiment in which more than four stiffening rods are used, a plurality of stiffening rods sufficient to substantially form a circle or perimeter around push/pull drive element may be used.

As illustrated in FIG. 8C, a conductive wire 770 extends on either side multi-lumen tube 744 and passes between multi-lumen tube 744 and an inner surface of shaft body 724 within passages 750 of shaft 706, through distal end cap 766, and into clevis 768, where each wire 770 connects to a respective electrode of the end effector 704. Conductive wires 770 connect to a power source at a backend or transmission mechanism (not shown) of bipolar surgical instrument 700. It should be understood that a shaft containing the non-conductive stiffening rods described below also may be used in a monopolar instrument. It also should be understood that in some cases drive rod 726 may be directly energized, rather than using conductive wire(s) 770.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary and elements within different embodiments may be used with one another. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings. Other embodiments in accordance with the present disclosure will be apparent to those skilled in the art from consideration of the specification. It is intended that the specification and examples be considered as exemplary only, with a true scope and spirit being indicated by the following claims.

What is claimed is:

1. A method of resisting axial compression in an instrument shaft, the method comprising:
    in response to application of a first force to the instrument shaft, placing a first stiffening element contained within the shaft and extending between first and second ends of the shaft under a first compressive force acting along an axial direction of the first stiffening element; and
    in response to application of a second force to the instrument shaft, subsequent to the application of the first force, placing a second stiffening element contained within the shaft and extending between the first and second ends of the instrument shaft under a second compressive force acting along an axial direction of the second stiffening element,
    wherein the second stiffening element is not placed under an axial force in response to application of the first force to the instrument shaft.

2. The method of claim 1, wherein placing the first stiffening element under the first compressive force occurs in response to bending the instrument shaft.

3. The method of claim 2, wherein bending the instrument shaft shortens a path between the first and second ends of the instrument shaft to place the first stiffening element under the first compressive force.

4. The method of claim 1, wherein application of the first force to the instrument shaft is caused by initiating actuation of an end effector of the instrument by transmitting force through a drive rod contained within the shaft.

5. The method of claim 4, wherein application of the second force is caused by continuing actuation of the end effector by transmitting force through the drive rod to a full actuation of the end effector.

6. The method of claim 5, wherein the continuing actuation applies the second force to the instrument shaft.

7. The method of claim 6, wherein the continuing actuation shortens a path between ends of the instrument shaft to place at least the second stiffening element under the second compressive force while the first stiffening element remains under at least the first compressive force.

8. The method of claim 4, further comprising, in response to actuating the end effector of the instrument with the drive rod, simultaneously placing the first stiffening element under the first compressive force and the second stiffening element under the second compressive force.

9. The method of claim 1, further comprising:
    during application of the first force, rotating the shaft about a longitudinal axis along the shaft; and
    in response to rotating the shaft about the longitudinal axis, unloading the first compressive force from being exerted on the first stiffening element and placing the second stiffening element under the first compressive force.

10. A medical instrument comprising:
    a shaft comprising a proximal end and a distal end;
    an end effector coupled to the distal end of the shaft;
    a first stiffening element extending in the shaft, the first stiffening element having a first length; and
    a second stiffening element extending in the shaft, the second stiffening element having a second length;
    wherein the first length is sufficient for the first stiffening element to absorb a portion of a first axial compression load applied to the shaft;
    wherein the second length is sufficient for the second stiffening element to absorb a portion of a second axial compression load applied to the shaft, the second axial compression load being larger than the first axial compression load; and
    wherein the second length is insufficient for the second stiffening element to absorb a portion of the first axial compression load.

11. The shaft of claim 10, wherein on the condition that the first axial compression load is applied to the shaft, the first stiffening element is under compressive force between the proximal and distal ends of the shaft.

12. The shaft of claim 10, wherein on the condition that the second axial compression load is applied to the shaft, the second stiffening element is under compressive force between the proximal and distal ends of the shaft.

13. The shaft of claim 10, further comprising:
    a third stiffening element extending in the shaft, the third stiffening element having a third length sufficient for the third stiffening element to absorb a portion of a third axial compression load applied to the shaft, the third length being insufficient for the third stiffening element to absorb a portion of the first and second axial loads;
    wherein a longitudinal axis of the shaft is defined between the proximal and distal ends of the shaft; and
    wherein the first, second, and third stiffening elements are equally spaced around the longitudinal axis of the shaft.

14. The shaft of claim 10, further comprising:
    a third stiffening element extending in the shaft, the third stiffening element having a third length sufficient for the third stiffening element to absorb a portion of a third axial compression load applied to the shaft, the third length being insufficient for the third stiffening element to absorb a portion of the first and second axial loads; and
    a fourth stiffening element extending in the shaft, the fourth stiffening element having a fourth length sufficient for the fourth stiffening element to absorb a portion of a fourth axial compression load applied to the shaft, the fourth length being insufficient for the fourth stiffening element to absorb a portion of the first, second, and third axial loads;
    wherein a longitudinal axis of the shaft is defined between the proximal and distal ends of the shaft; and
    wherein the first, second, third, and fourth stiffening elements are equally spaced around the longitudinal axis of the shaft.

15. The shaft of claim 10, further comprising a multi-lumen tube extending through the shaft, wherein each of the first stiffening element and the second stiffening element extend through individual lumens of the multi-lumen tube.

16. The shaft of claim 15, wherein the multi-lumen tube has a first length shorter than the first length of the first stiffening element and shorter than the second length of the second stiffening element.

17. The shaft of claim 10, wherein the first length of the first stiffening element and the second length of the second stiffening element are equal.

18. The shaft of claim 10, wherein on the condition that the first and second axial compression loads are not applied to the shaft, at least one of the first stiffening element and the second stiffening element are free to move longitudinally within the shaft.

19. The shaft of claim 10, wherein the first stiffening element and the second stiffening element each comprise a non-conductive material.

* * * * *